United States Patent
Harris et al.

(10) Patent No.: US 10,758,231 B2
(45) Date of Patent: Sep. 1, 2020

(54) SURGICAL STAPLER WITH BENT ANVIL TIP, ANGLED STAPLE CARTRIDGE TIP, AND TISSUE GRIPPING FEATURES

(71) Applicant: ETHICON LLC, Guaynabo, PR (US)

(72) Inventors: Jason L. Harris, Lebanon, OH (US); Daniel L. Baber, Cincinnati, OH (US); Joseph P. Schowalter, South Lebanon, OH (US); Gregory J. Bakos, Mason, OH (US); Frederick E. Shelton, IV, Hillsboro, OR (US)

(73) Assignee: Ethicon LLC, Guaynabo, PR (US)

( * ) Notice: Subject to any disclaimer, the term of this patent is extended or adjusted under 35 U.S.C. 154(b) by 441 days.

(21) Appl. No.: 15/435,631

(22) Filed: Feb. 17, 2017

(65) Prior Publication Data
US 2018/0235619 A1 Aug. 23, 2018

(51) Int. Cl.
*A61B 17/072* (2006.01)
*A61B 17/068* (2006.01)
*A61B 90/00* (2016.01)

(52) U.S. Cl.
CPC .... *A61B 17/07207* (2013.01); *A61B 17/0686* (2013.01); *A61B 2017/07221* (2013.01); *A61B 2017/07228* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2090/0807* (2016.02)

(58) Field of Classification Search
CPC ........... A61B 2017/07214; A61B 2017/07221; A61B 2017/07257; A61B 2017/07271
See application file for complete search history.

(56) References Cited

U.S. PATENT DOCUMENTS

| | | | |
|---|---|---|---|
| 4,805,823 A | 2/1989 | Rothfuss | |
| 5,300,087 A * | 4/1994 | Knoepfler | A61B 17/29 604/33 |

(Continued)

FOREIGN PATENT DOCUMENTS

| | | |
|---|---|---|
| EP | 2 913 010 A2 | 9/2015 |
| EP | 3 123 950 A1 | 2/2017 |
| WO | WO 2004/096057 A2 | 11/2004 |

OTHER PUBLICATIONS

European Search Report and Written Opinion dated Apr. 26, 2018 for Application No. EP 18157174.6, 10 pgs.

(Continued)

*Primary Examiner* — Nathaniel C Chukwurah
*Assistant Examiner* — Lucas E. A. Palmer
(74) *Attorney, Agent, or Firm* — Frost Brown Todd LLC

(57) ABSTRACT

A surgical instrument includes a body portion, a shaft, and an end effector that is operable to compress, staple, and cut tissue. The end effector includes an anvil and a staple cartridge. The anvil has a rigid bent tip configured to contact an angled surface of a nose portion of the staple cartridge. The staple cartridge includes gripping features along a staple deck that assist in gripping tissue during clamping. The staple deck of the cartridge may include multiple levels. The anvil further includes a slot with lateral portions having curved ends for receiving portions of a firing beam to guide the firing beam during a cutting and stapling action.

20 Claims, 20 Drawing Sheets

(56) References Cited

U.S. PATENT DOCUMENTS

| | | | |
|---|---|---|---|
| 5,397,324 A * | 3/1995 | Carroll | A61B 17/07207 128/898 |
| 5,403,312 A * | 4/1995 | Yates | A61B 17/07207 606/50 |
| 5,415,334 A | 5/1995 | Williamson et al. | |
| 5,452,837 A * | 9/1995 | Williamson, IV | A61B 17/07207 227/176.1 |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitma et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 9,186,142 B2 | 11/2015 | Fanelli et al. | |
| 9,301,759 B2 | 4/2016 | Spivey et al. | |
| 9,517,065 B2 | 12/2016 | Simms et al. | |
| D836,198 S | 12/2018 | Harris et al. | |
| 2004/0243151 A1 * | 12/2004 | Demmy | A61B 17/068 606/139 |
| 2005/0119669 A1 * | 6/2005 | Demmy | A61B 17/068 606/139 |
| 2008/0237297 A1 * | 10/2008 | Demmy | A61B 17/07207 227/176.1 |
| 2008/0269793 A1 * | 10/2008 | Scirica | A61B 17/07207 606/190 |
| 2009/0209946 A1 * | 8/2009 | Swayze | A61B 17/07207 606/1 |
| 2010/0094315 A1 * | 4/2010 | Beardsley | A61B 17/07207 606/143 |
| 2011/0186614 A1 * | 8/2011 | Kasvikis | A61B 17/07207 227/175.2 |
| 2012/0143218 A1 * | 6/2012 | Beardsley | A61B 17/07207 606/142 |
| 2012/0199628 A1 * | 8/2012 | Scirica | A61B 17/07207 227/175.1 |
| 2013/0146642 A1 * | 6/2013 | Shelton, IV | A61B 17/068 227/177.1 |
| 2014/0110456 A1 * | 4/2014 | Taylor | A61B 17/072 227/176.1 |
| 2014/0239036 A1 * | 8/2014 | Zerkle | A61B 17/07207 227/175.1 |
| 2014/0239037 A1 | 8/2014 | Boudreaux et al. | |
| 2014/0239038 A1 | 8/2014 | Leimbach et al. | |
| 2014/0239041 A1 | 8/2014 | Zerkle | |
| 2014/0239042 A1 * | 8/2014 | Simms | A61B 17/07207 227/176.1 |
| 2014/0239043 A1 * | 8/2014 | Simms | A61B 17/07207 227/176.1 |
| 2014/0239044 A1 | 8/2014 | Hoffman | |
| 2015/0173761 A1 * | 6/2015 | Shelton, IV | A61B 17/07207 227/177.1 |
| 2015/0216528 A1 * | 8/2015 | Demmy | A61B 17/07207 606/139 |
| 2015/0272575 A1 | 10/2015 | Leimbach et al. | |
| 2015/0374361 A1 * | 12/2015 | Gettinger | A61B 17/068 227/175.2 |
| 2015/0374363 A1 * | 12/2015 | Laurent, IV | A61B 17/068 227/175.3 |
| 2015/0374373 A1 * | 12/2015 | Rector | A61B 17/0644 606/219 |

OTHER PUBLICATIONS

International Search Report and Written Opinion dated Apr. 26, 2018 for Application No. PCT/US2018/017931, 14 pgs.
U.S. Appl. No. 15/435,573, filed Feb. 17, 2017.
U.S. Appl. No. 15/435,607, filed Feb. 17, 2017.
U.S. Appl. No. 15/435,618, filed Feb. 17, 2017.
Design U.S. Appl. No. 29/594,335, filed Feb. 17, 2017.
Design U.S. Appl. No. 29/594,340, filed Feb. 17, 2017.

* cited by examiner

SURGICAL STAPLER WITH BENT ANVIL TIP, ANGLED STAPLE CARTRIDGE TIP, AND TISSUE GRIPPING FEATURES

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued as U.S. Pat. No. 8,408,439 on Apr. 2, 2013; and U.S. Pub. No. 2012/0239012, entitled "Motor-Driven Surgical Cutting Instrument with Electric Actuator Directional Control Assembly," published Sep. 20, 2012, issued as U.S Pat. No. 8,453,914 on Jun. 4, 2013. The disclosure of each of the above-cited U.S. patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
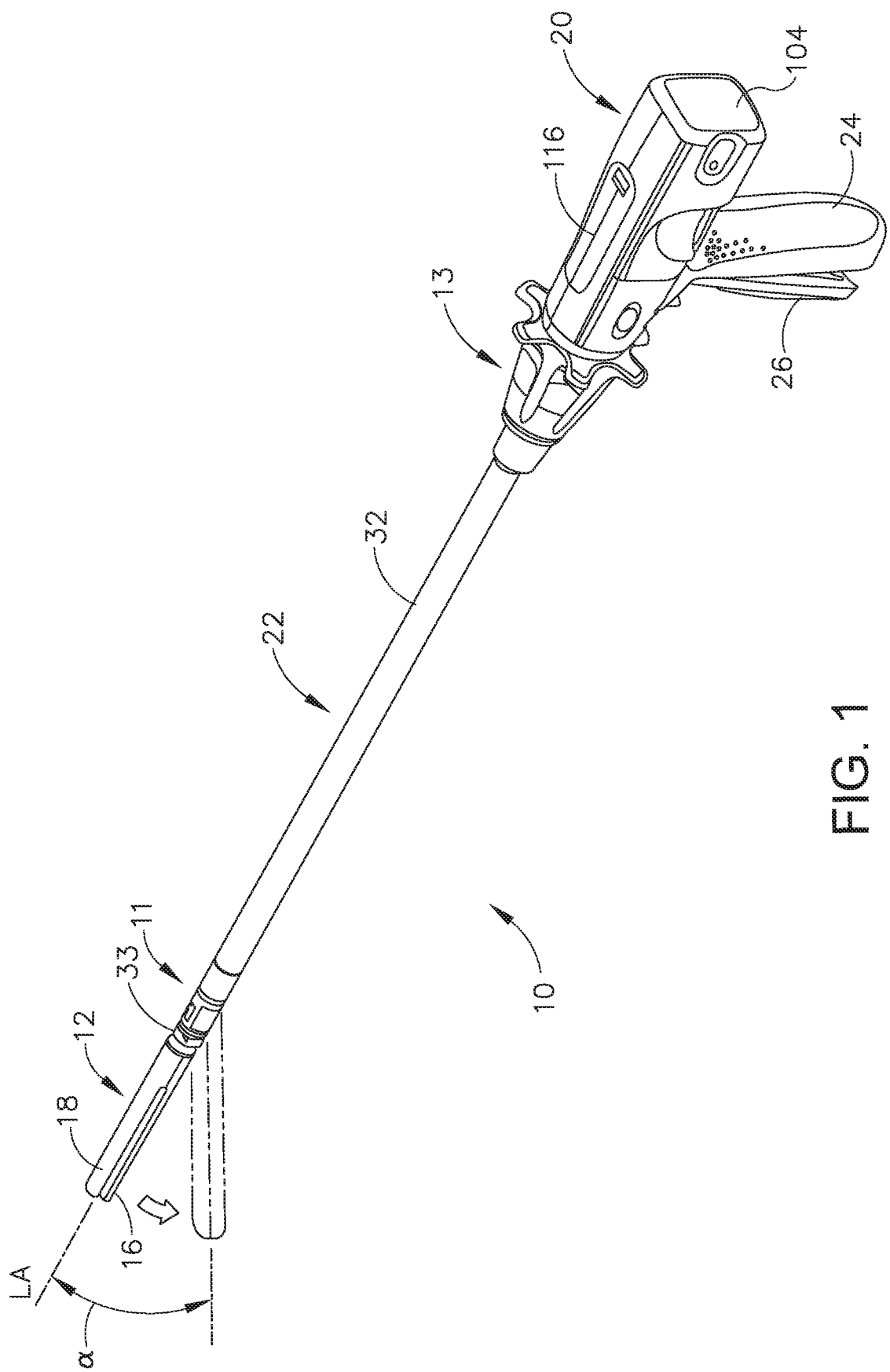
FIG. 1 depicts a perspective view of an exemplary articulating surgical stapling instrument.
Figure 2:
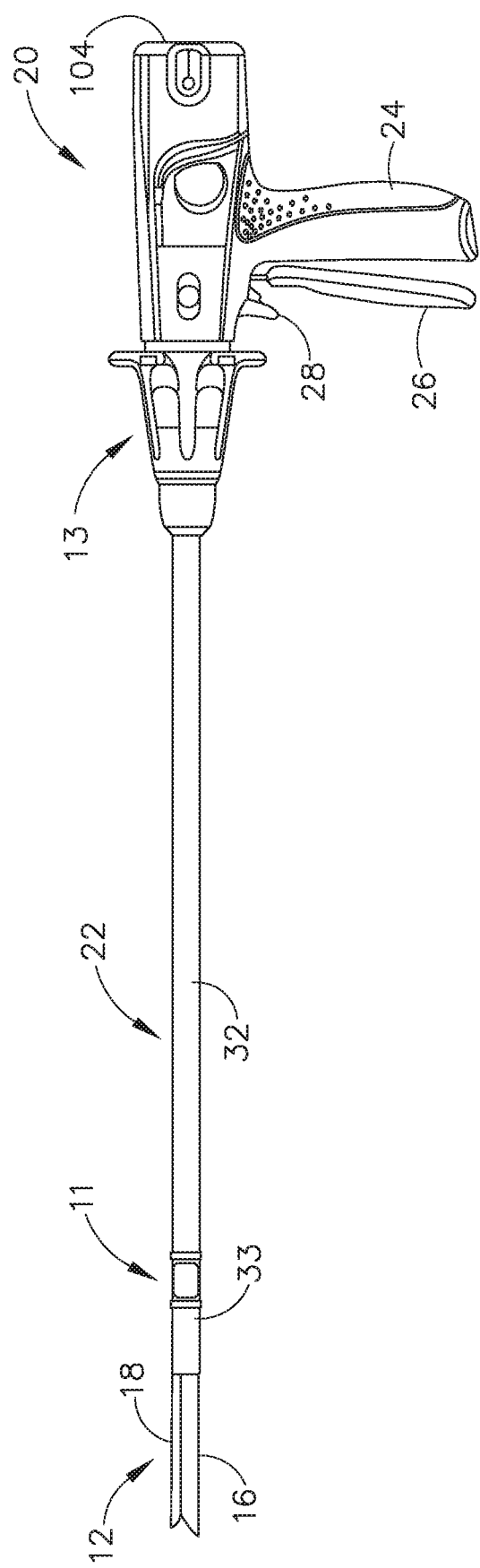
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. By way of further example only, shaft (22) may be detachable from handle portion (20) in accordance with at least some of the teachings of U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein. In some other versions, shaft (22) is not detachable from handle portion (20). Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. Pub. No. 2014/0239044, entitled "Installation Features for Surgical Instrument End Effector Cartridge," published on Aug. 28, 2014, issued as U.S. Pat. No. 9,808,248 on Nov. 7, 2017, the disclosure of which is incorporated by reference herein. Anvil (18) may be constructed in accordance with at least some of the teachings of U.S. Pub. No. 2014/0239042, entitled "Integrated Tissue Positioning and Jaw Alignment Features for Surgical Stapler," published on Aug. 28, 2014, issued as U.S. Pat. No. 9,517,065 on Dec. 13, 2016, the disclosure of which is incorporated by reference herein; at least some of the teachings of U.S. Pub. No. 2014/0239036, entitled "Jaw Closure Feature for End Effector of Surgical Instrument," published on Aug. 28, 2014, issued as U.S. Pat. No. 9,839,421 on Dec. 12, 2017, the disclosure of which is incorporated by reference herein; and/or at least some of the teachings of U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pub. No. 2014/0239041, entitled "Lockout Feature for Movable Cutting Member of Surgical Instrument," published on Aug. 28, 2014, issued as U.S. Pat. No. 9,717,497 on Aug. 1, 2017, the disclosure of which is incorporated by reference herein. Other suitable forms that firing beam (14) may take will be apparent to those of ordinary skill in the art in view of the teachings herein.

Figure 3:
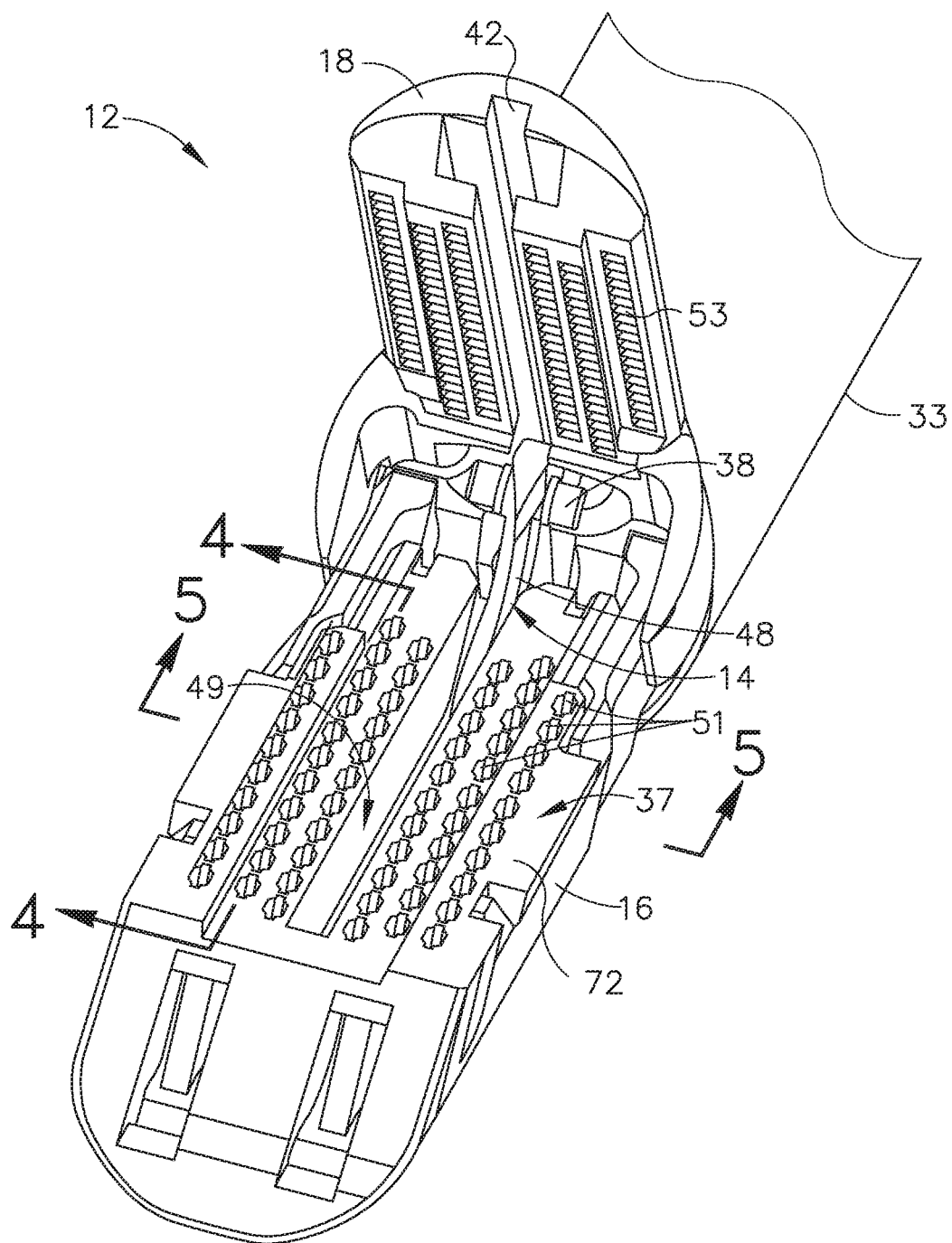
FIG. 3 depicts a perspective view of an opened end effector of the instrument of FIG. 1.
Figure 4A:
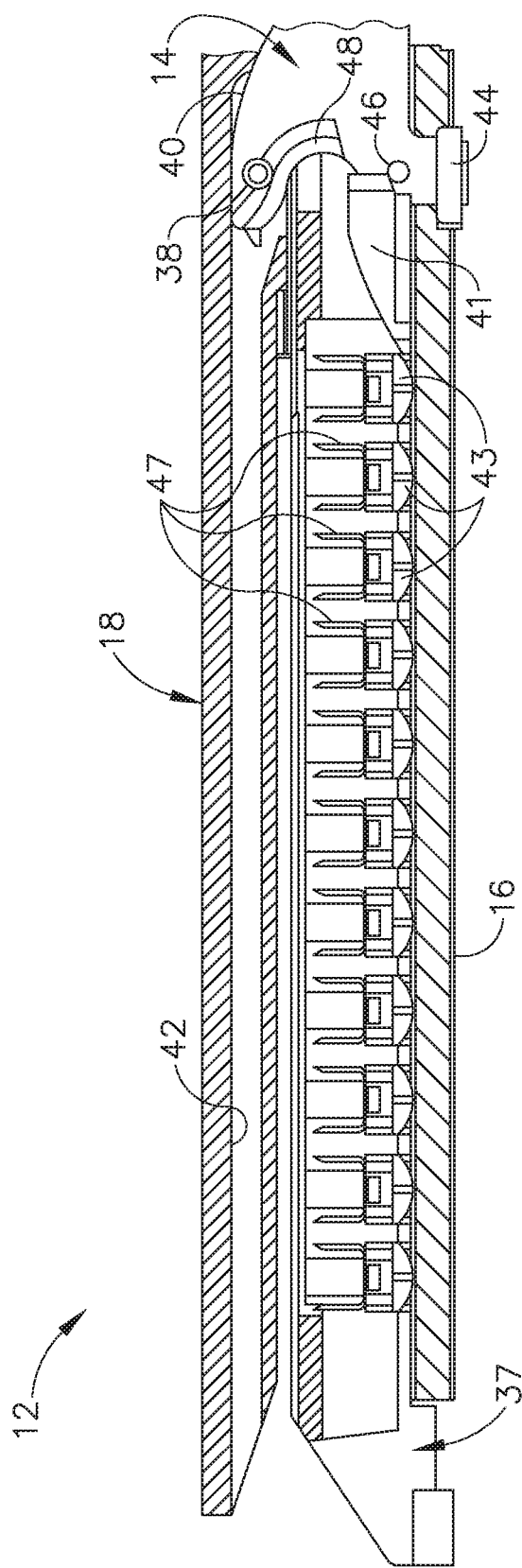
FIG. 4A depicts a side cross-sectional view of the end effector of FIG. 3, taken along line 4-4 of FIG. 3, with the firing beam in a proximal position.
Figure 4B:
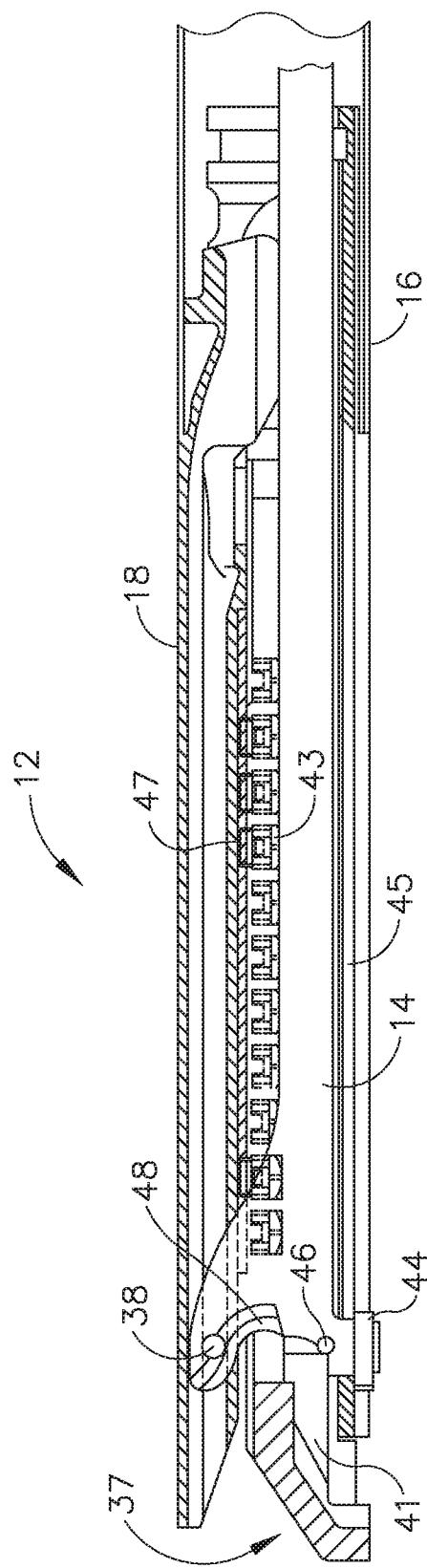
FIG. 4B depicts a side cross-sectional view of the end effector of FIG. 3, taken along line 4-4 of FIG. 3, with the firing beam in a distal position.
Figure 5:
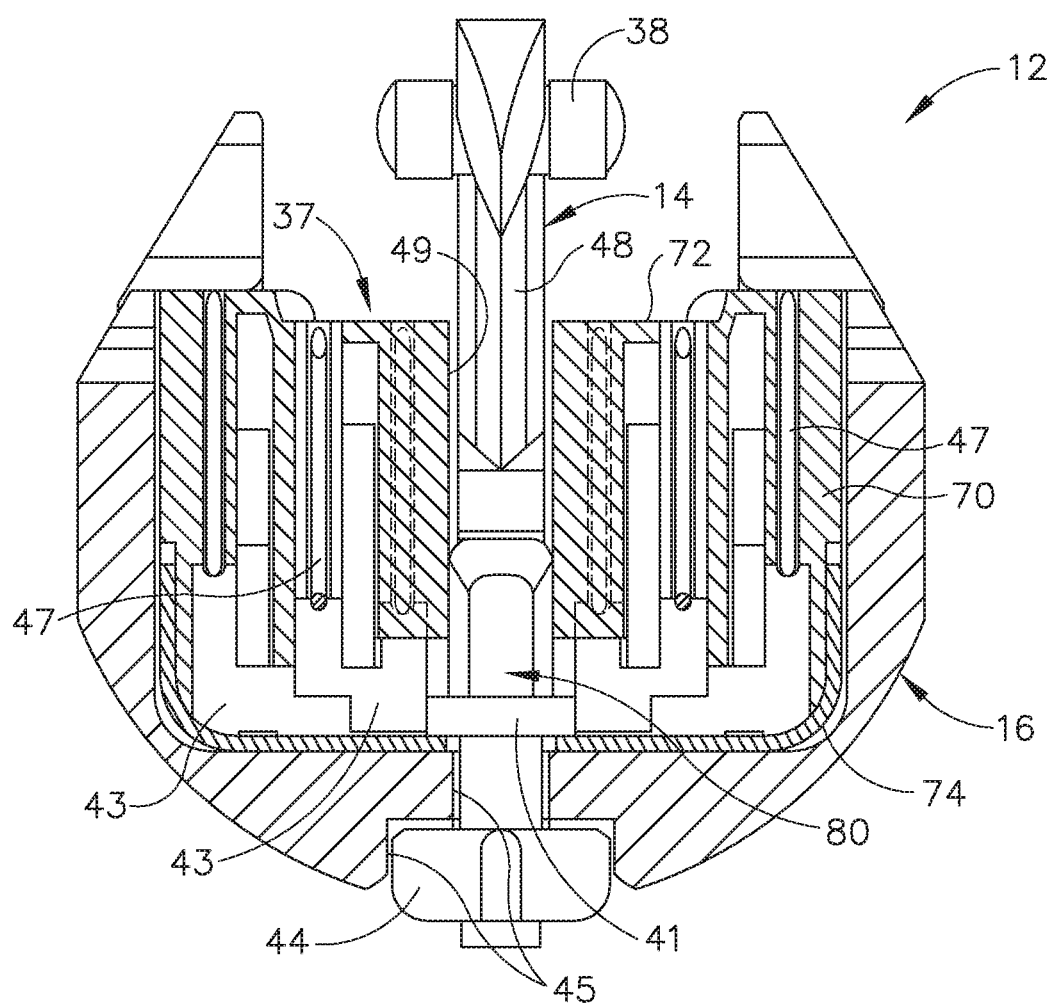
FIG. 5 depicts an end cross-sectional view of the end effector of FIG. 3, taken along line 5-5 of FIG. 3.
Figure 6:
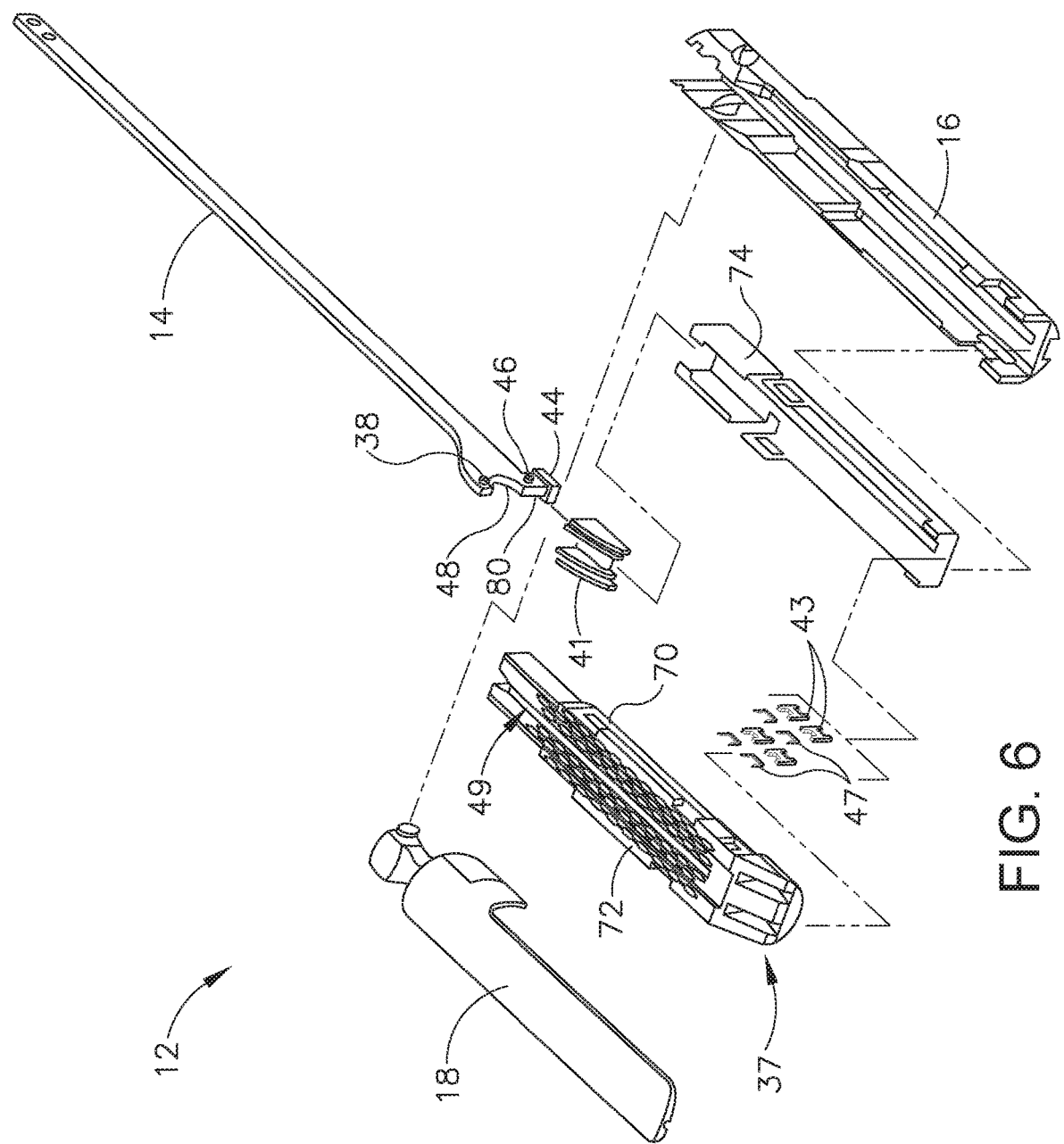
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pub. No. 2014/0239042, entitled "Integrated Tissue Positioning and Jaw Alignment Features for Surgical Stapler," published on Aug. 28, 2014, issued as U.S. Pat. No. 9,517,065 on Dec. 13, 2016, the disclosure of which is incorporated by reference herein. In addition or in the alternative, staple cartridge (37) may be constructed and operable in accordance with at least some of the teachings of U.S. Pub. No. 2014/0239044, entitled "Installation Features for Surgical Instrument End Effector Cartridge," published on Aug. 28, 2014, issued as U.S. Pat. No. 9,808,248 on Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
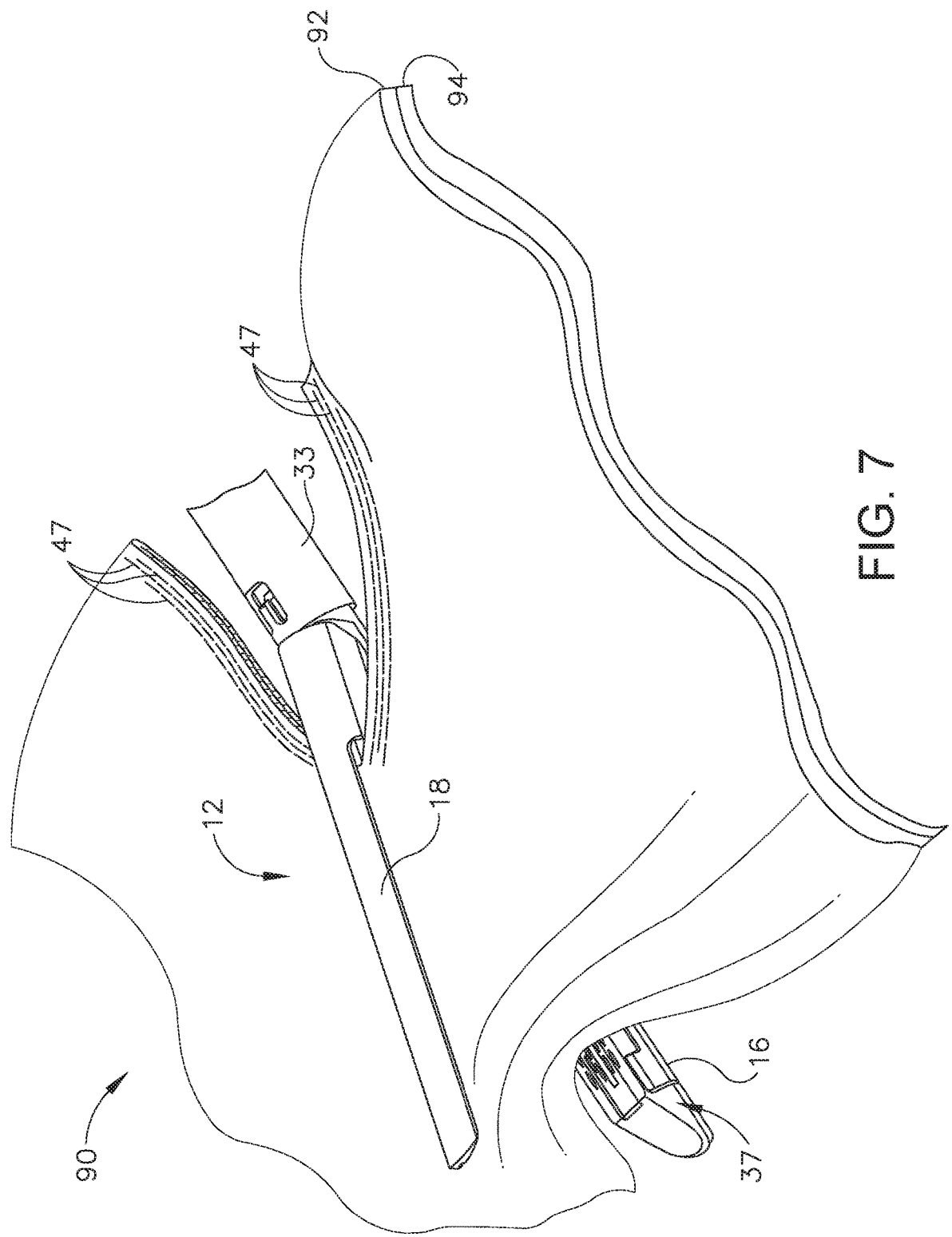
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in US. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pub. No. 2012/0239012, issued as U.S. Pat. No. 8,453,914 on Jun. 4, 2013, the disclosure of which is incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in US. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; U.S. Pub. No. 2010/0264193, issued as U.S. Pat. No. 8,408,439 on Apr. 2, 2013; and/or 2012/0239012, issued as U.S. Pat. No. 8,453,914 on Jun. 4, 2013. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effector with Visualization, Lead-In, and Gathering Feature In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
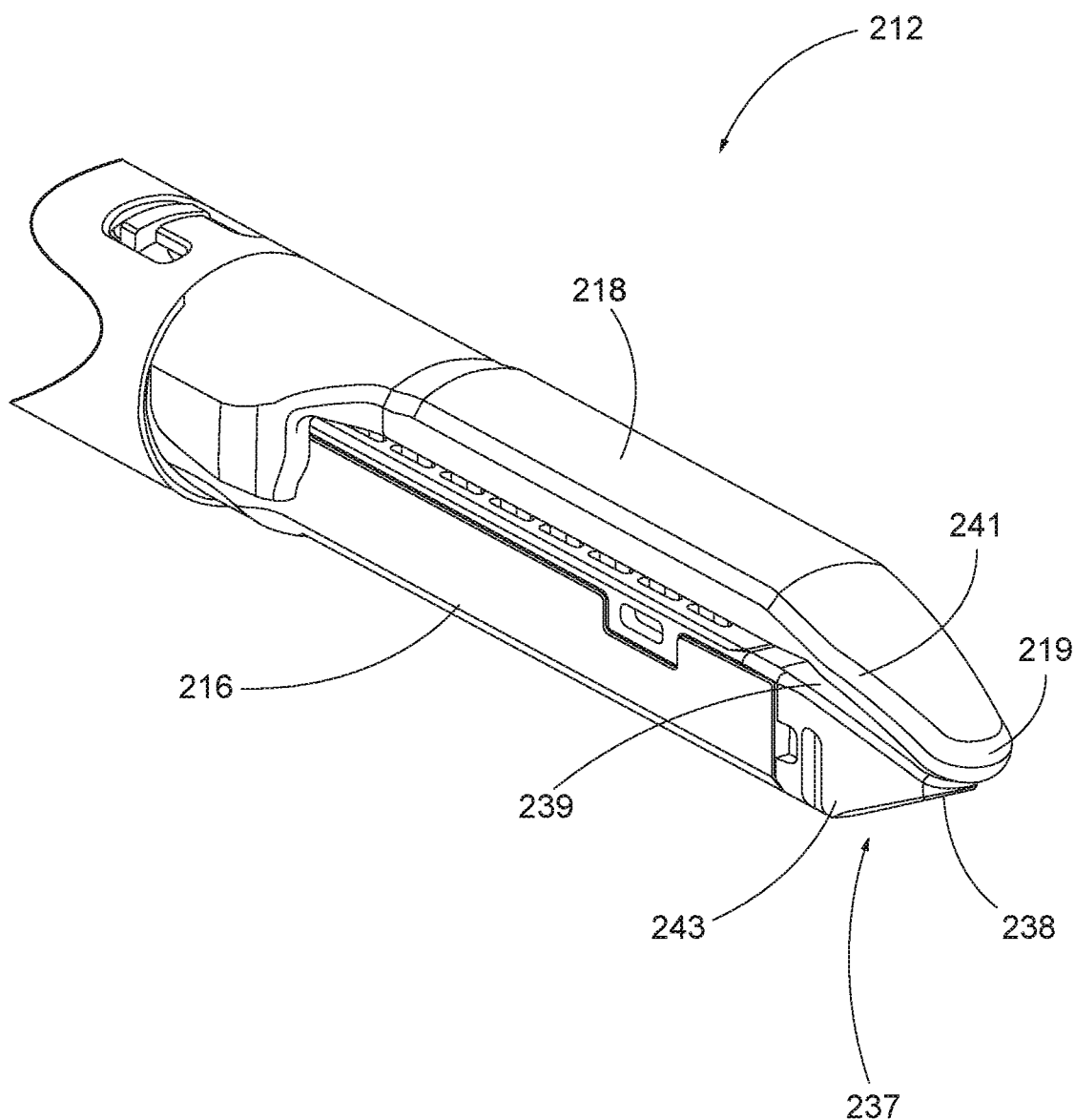
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
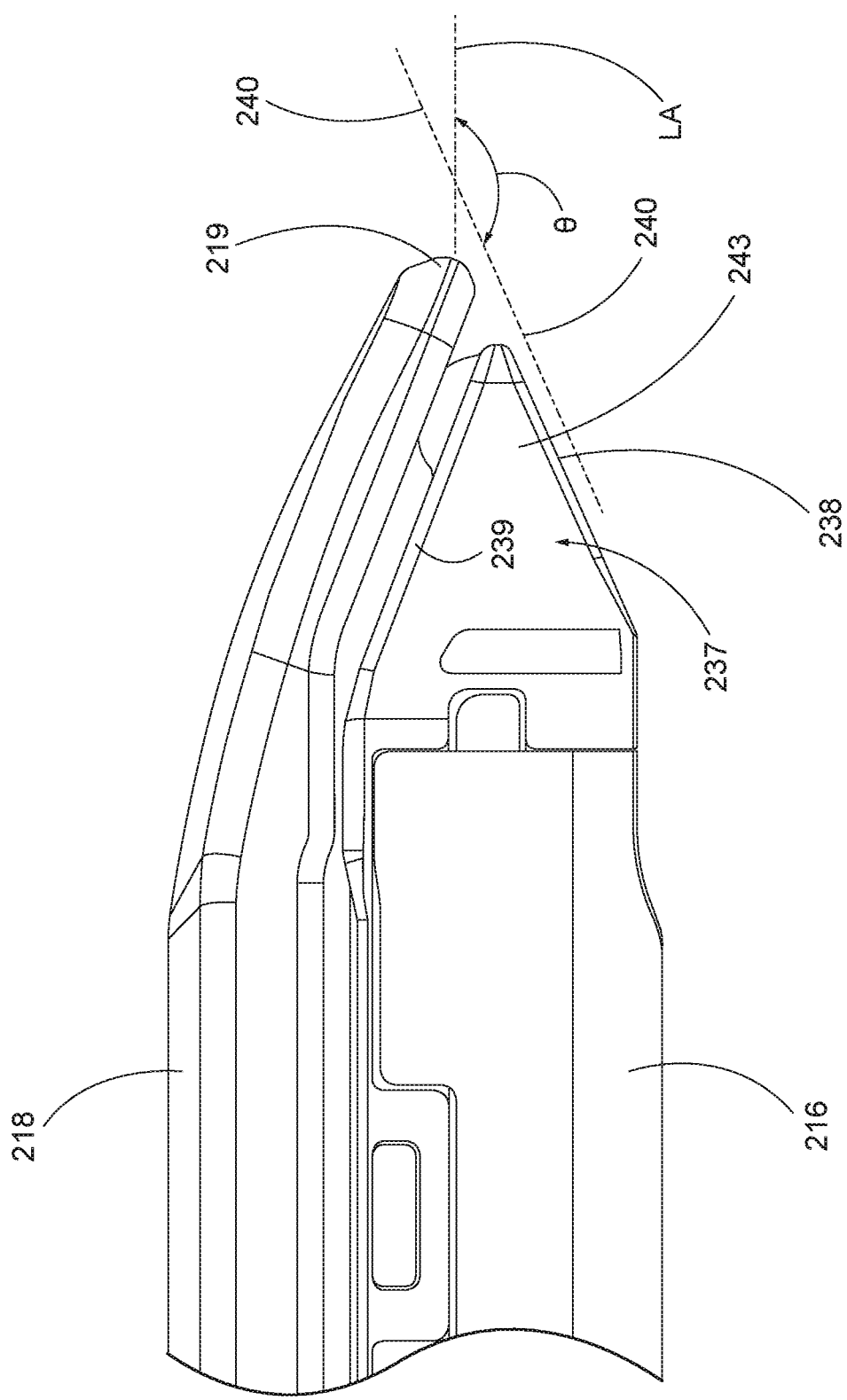
FIG. 9 depicts an enlarged, side view of the end effector of FIG. 8.
Figure 10:
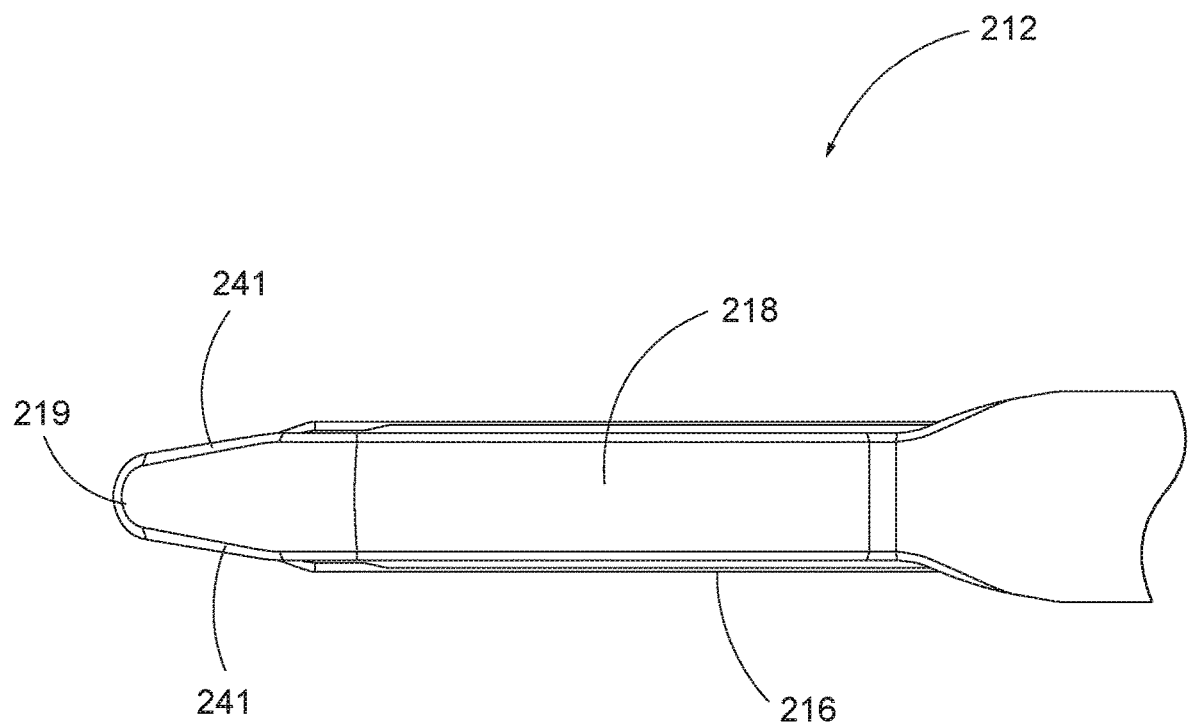
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle ($\theta$).

Viewing angle ($\theta$) may establish the relative visibility that a user has regarding distal tip (219). In particular, the user can see in front of distal tip (219) along any line of sight that passes through the intersection of sight line (240) and longitudinal axis (LA) within viewing angle ($\theta$). For instance, as viewing angle ($\theta$) increases, the user would have greater visibility of the area immediately in front of distal tip (219) from proximal vantage points; whereas as viewing angle ($\theta$) decreases, the user has less visibility of the area in front of distal tip (219) from proximal vantage points. In some versions, viewing angle ($\theta$) defines an angle greater than 90 degrees. Additionally, in some versions, viewing angle ($\theta$) defines an angle greater than 135 degrees. Other suitable angles for viewing angle ($\theta$) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90).

It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pub. No. 2014/0239041, entitled "Lockout Feature for Movable Cutting Member of Surgical Instrument," published Aug. 28, 2014, issued as U.S. Pat. No. 9,717,497 on Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; U.S. Pub. No. 2014/0239043, entitled "Distal Tip Features for End Effector of Surgical Instrument," published Aug. 28, 2014, issued as U.S. Pat. No. 9,622,746 on Apr. 18, 2017, the disclosure of which is incorporated by reference herein; U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein; and/or U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Further modifications that may be incorporated into end effector (212) will be described in greater detail below.

III. Exemplary End Effector with Rigid Bent Anvil Tip

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). In some instances, it may be desirable to provide an end effector that has an anvil bent distal end configuration similar to that of anvil (218); while also having a cartridge with a distal end configuration similar to that of cartridge (37). By providing a hybrid end effector having an anvil similar to anvil (218) and a cartridge similar to cartridge (37), the bent distal portion of the anvil may have a relatively steeper bend angle, which may further promote tissue gathering effects as described herein. The following description provides examples of end effectors that combine structural aspects of anvil (218) and structural aspects of cartridge (37), along with other structural features.

A. Exemplary Anvil and Cartridge Orientation

Figure 11:
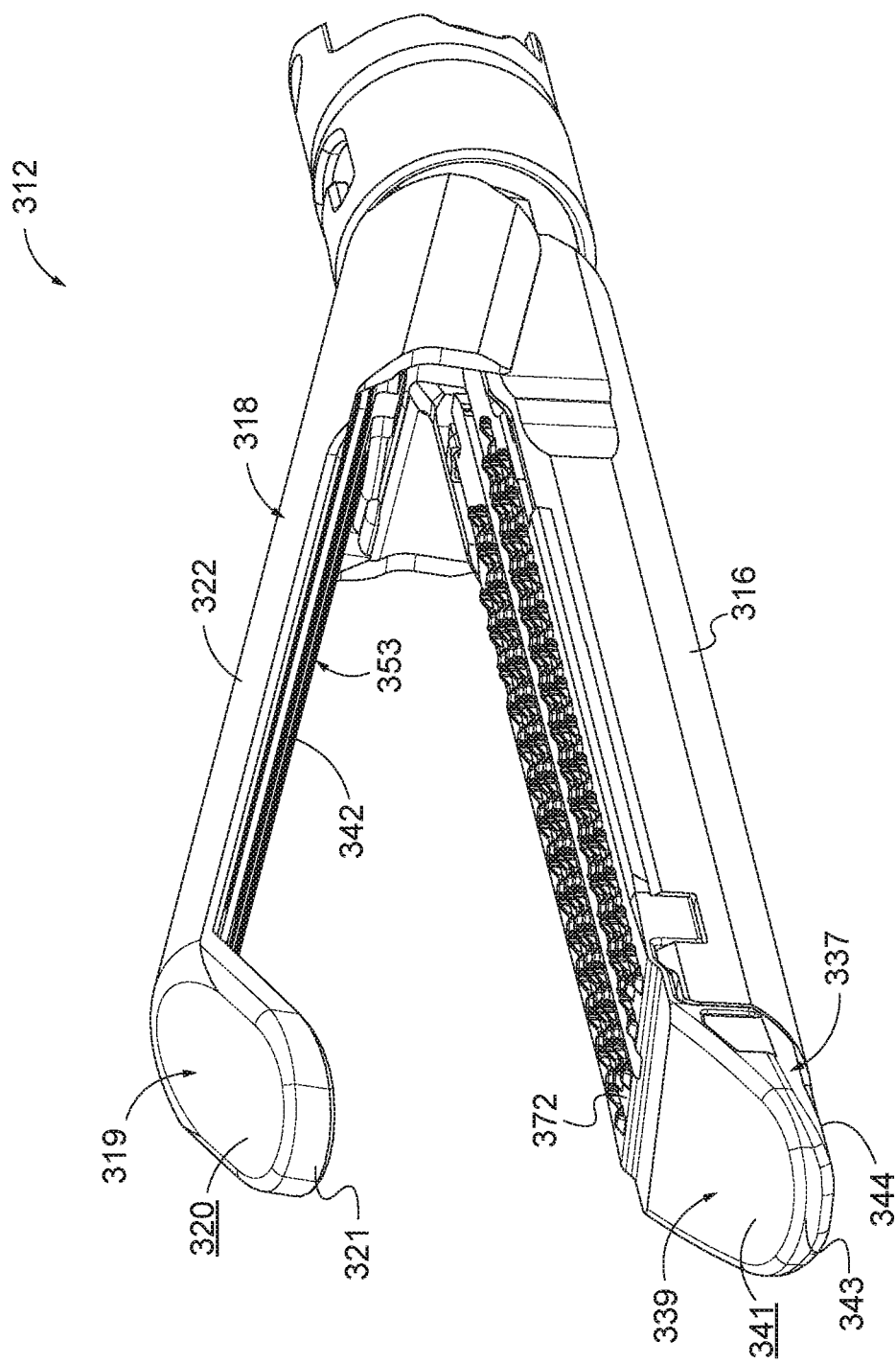
FIG. 11 depicts a perspective view of a distal portion of another alternative version of an end effector, with a curved anvil tip, shown in an open configuration.
Figure 12:
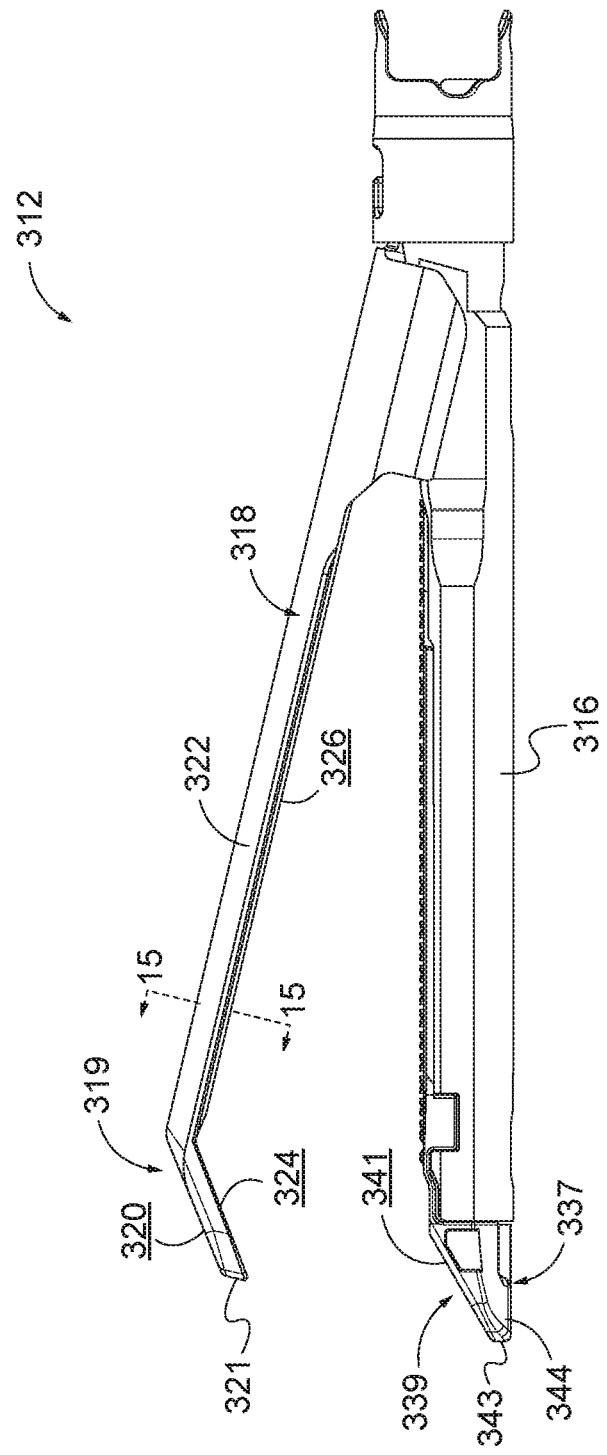
FIG. 12 depicts a side view of the end effector of FIG. 11.
Figure 13:
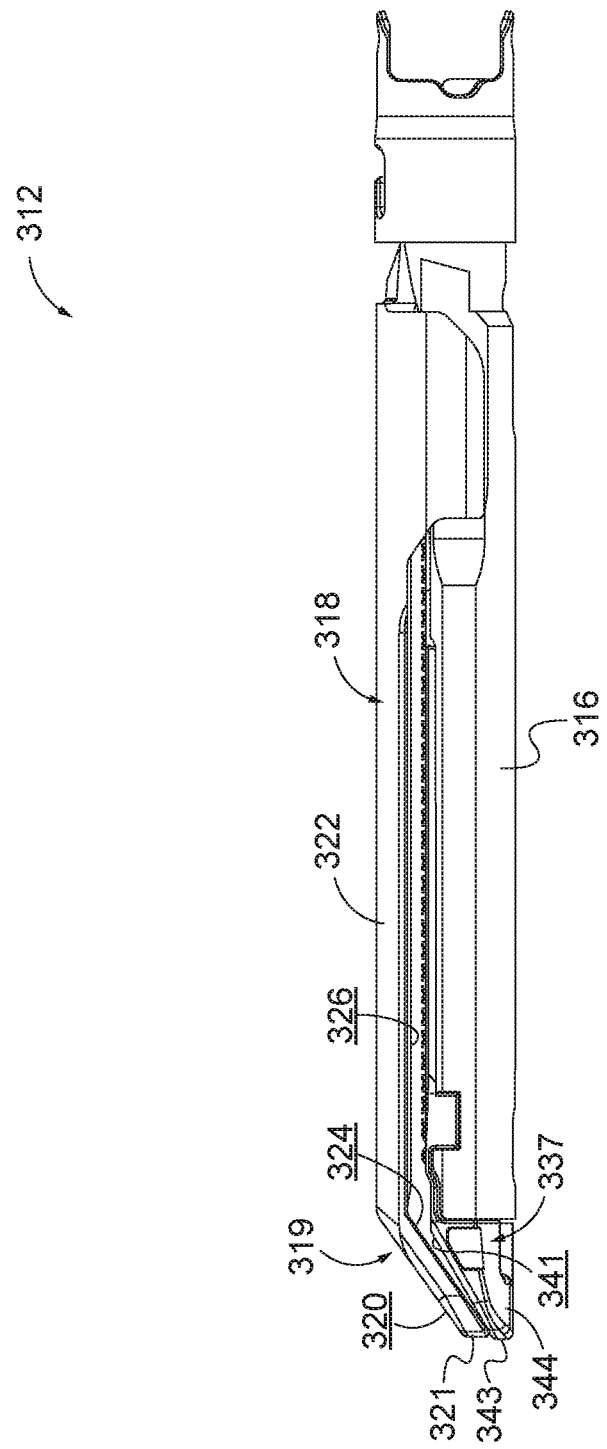
FIG. 13 depicts a side view of the end effector of FIG. 11, but shown in the closed configuration.

FIGS. 11-13 depict an exemplary end effector (312) comprising an anvil (318) and a lower jaw (316). It will be appreciated that end effector (312) may be used in place of end effector (12) of instrument (10). End effector (312) may be integrally formed with instrument (10) or in the alternative may be interchangeable with end effector (12) of instrument (10). Anvil (318) is operable to pivot relative to lower jaw (316). Anvil (318) and lower jaw (316) may clamp tissue (90) similarly to clamping performed by anvil (18) and lower jaw (16) shown in FIG. 1. End effector (312) further comprises a cartridge (337) that is operable to be placed in lower jaw (316) similarly to cartridge (37) shown in FIG. 3.

Anvil (318) comprises staple forming pockets (353), which are similar to staple forming pockets (53) of anvil (18). Anvil (318) further comprises anvil slot (342), which is similar to anvil slot (42) of anvil (18). Anvil (318) differs from anvil (18) in that anvil (318) comprises a bent tip (319) at its distal end. As used herein, terms such as "bent," "angled," and "curved" shall be read as being synonymous with each other when referring to a distal end configuration of a component of an end effector. In other words, the terms "bent" and "curved" (and variations thereof) may include a relationship between two straight features that together define an angle, such that the terms "bent" and "curved" (and variations thereof) should not be read as requiring a component to necessarily extend along an arc. In the present example, tip (319) is non-deflectable and thus tip (319) maintains its shape. Described another way, tip (319) in the present example is rigid. In the present example, anvil (318) and associated tip (319) are constructed from metal, although other materials such as plastic, ceramic, and others may be used as will be apparent to those of ordinary skill in the art in view of the teachings herein.

Tip (319) comprises an outer surface (320) with a blunt end (321). Proximal to tip (319), anvil (318) comprises a body portion (322) that extends in a straight manner. In the illustrated example, body portion (322) forms the majority of anvil (318) such that the majority of anvil (318) is straight. Referring to FIG. 12, anvil (318) further comprises an inner surface (324) along tip (319), and an underside surface (326) along body portion (322) where staple forming pockets (353) are located. In the present example, with tip (319) having a bent or angled configuration, outer surface (320) and inner surface (324) are angled relative to straight body portion (322) and underside surface (326) of anvil (318).

Figure 14:
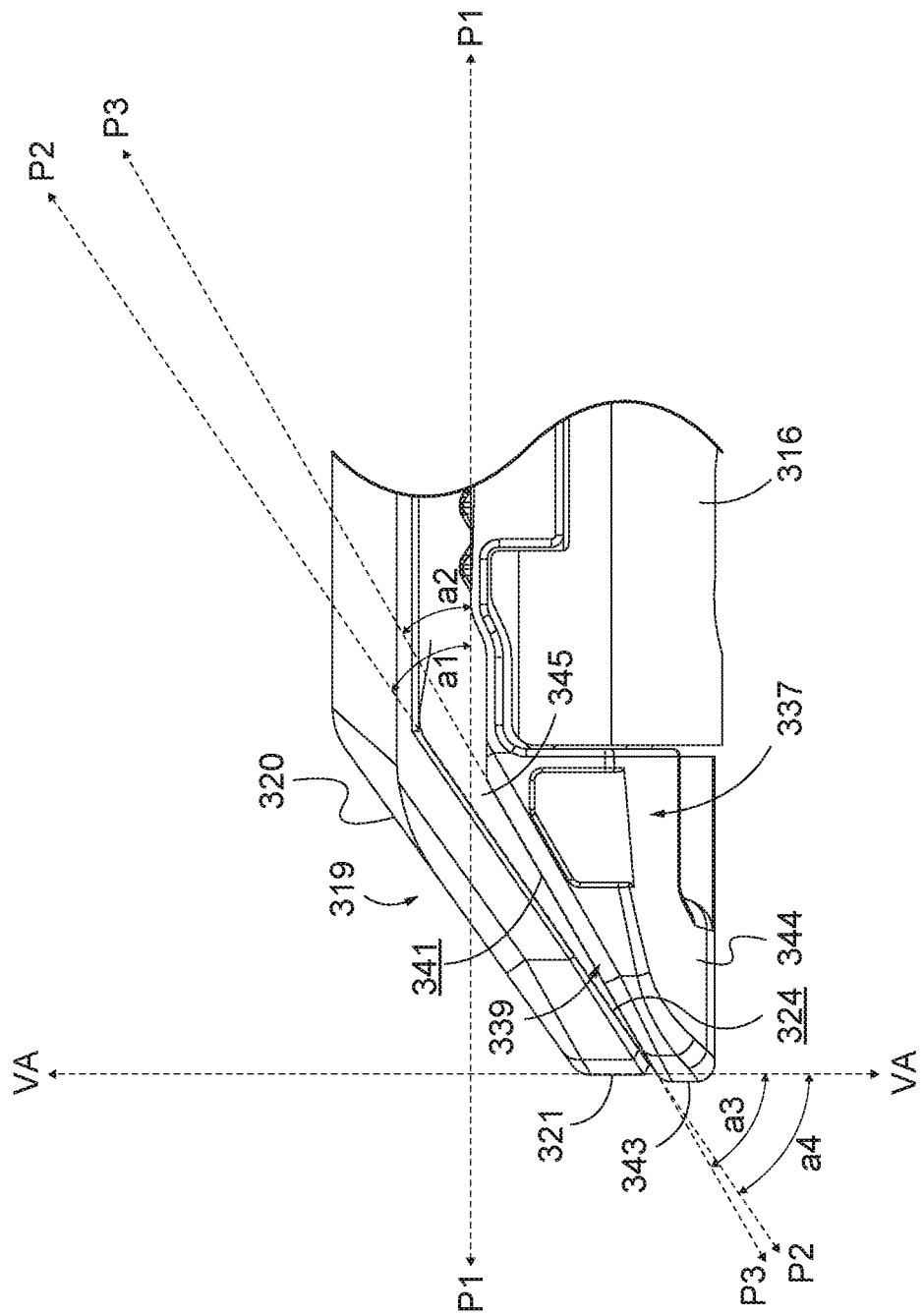
FIG. 14 depicts an enlarged side view of the distal portion of the end effector of FIG. 13.

Cartridge (337) of end effector (312) comprises distal tip (339). Tip (339) comprises angled surface (341), blunt end (343), and curved underside (344). As shown in FIGS. 13 and 14, when end effector (312) is closed, blunt end (321) is longitudinally positioned evenly with blunt end (343) of cartridge (337). In this manner, blunt end (321) and blunt end (343) terminate at the same longitudinal position (e.g., such that blunt end (321) and blunt end (343) terminate at the same plane extending perpendicularly through the longitudinal axis of end effector (312). In view of the teachings herein, it will be apparent to those of ordinary skill in the art that in other examples, blunt end (321) may be located proximally relative to blunt end (343) of cartridge (337) when end effector (312) is closed. Similarly, in some other examples end effector (312) may be configured such that blunt end (321) of anvil (318) extends distally relative to blunt end (343) of cartridge (337) when end effector (312) is closed. Also in view of the teachings herein, it will be apparent to those of ordinary skill in the art that in other examples, one or both of blunt ends (321, 343) may be modified such that they do not have a blunt configuration, or that they may not have a blunt configuration and may be protected by a blunt cover or shield.

FIG. 14 illustrates an enlarged view of the distal end of end effector (312), shown in the closed position. As shown, in the closed position inner surface (324) partially contacts angled surface (341) at the distal end of end effector (312). Further proximally along inner surface (324) and angled surface (341), there is a gap or space (345) between inner surface (324) and angled surface (341) when end effector (312) is closed. As shown in FIG. 11, cartridge (337) comprises an upper deck (372). As illustrated in FIG. 14, upper deck (372) defines a plane (P1). Similarly, inner surface (324) defines a plane (P2), and angled surface (341) defines a plane (P3). As also shown in FIG. 14, the distal end of end effector (312) defines a vertical axis (VA). Vertical axis (VA) is generally orthogonal to plane (P1) defined by upper deck (372).

Referring to FIG. 14, with the configuration described above, where inner surface (324) partially contacts angled surface (341) when end effector (312) is closed, inner surface (324) is steeper compared to angled surface (341) relative to vertical axis (VA). For instance, this is shown by angle (a4) formed at the intersection of plane (P2) with vertical axis (VA) being smaller or less compared to angle (a3) formed at the intersection of plane (P3) with vertical axis (VA). This steeper orientation associated with inner surface (324) compared to angled surface (341) is also shown by angle (a1) formed at the intersection of plane (P2) with plane (P1) being smaller or less compared to angle (a2) formed at the intersection of plane (P3) with plane (P1).

In the present example, inner surface (324) forms angle (a1) of about 35 degrees with plane (P1), which is the plane defined by upper deck (372) as described above. Comparatively, angled surface (341) forms angle (a2) of about 25 degrees with plane (P1). Thus in the present example, inner surface (324) forms or defines angle (a1) with plane (P1) of about 10 degrees more than angle (a2) formed or defined by angled surface (341) and plane (P1). Conversely, this could be stated that angled surface (341) forms or defines angle (a2) with plane (P1) of about 10 degrees less than angled (a1) formed or defined by inner surface (324) and plane (P1).

Also in the present example, inner surface (324) forms an angle (a4) of about 55 degrees with vertical axis (VA), which is the axis defined by the distal end of end effector (312) as described above. Comparatively, angled surface (341) forms an angle (a3) of about 65 degrees with vertical axis (VA). Thus in the present example, inner surface (324) forms or defines angle (a4) with vertical axis (VA) of about 10 degrees less than angle (a3) formed or defined by angled surface (341) and vertical axis (VA). Conversely, this could be stated that angled surface (341) forms or defines angle (a3) with vertical axis (VA) of about 10 degrees more than angle (a4) formed or defined by inner surface (324) and vertical axis (VA). In view of the teachings herein, various modifications to tips (319, 339) to modify the angles described above will be apparent to those of ordinary skill in the art.

B. Exemplary Anvil Longitudinal Slots and Underside Surface

In some instances, with anvils having bent tips, certain modifications can be made to the slots and underside surface of the anvil to provide for possible enhancements to the cutting and stapling. Some such modifications or modified anvils are described below, and others will be apparent to those of ordinary skill in the art in view of the teachings herein.

Figure 15:
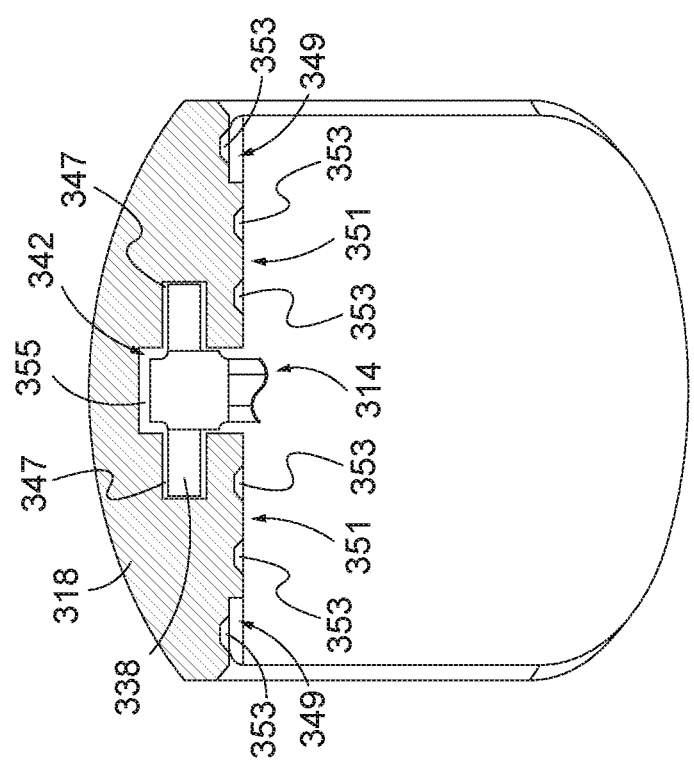
FIG. 15 depicts a cross-sectional view of the anvil of the end effector of FIG. 11, taken along line 15-15 of FIG. 12.

FIG. 15 depicts a section view of anvil (318) that illustrates anvil slot (342). As shown, slot (342) comprises a partial "I" shape in cross section. In this manner, slot (342) comprises lateral portions (347) and top hat portion (355). Firing beam (314), which is similar to firing beam (14) described above, is positionable within slot (342) in the same manner as firing beam (14) is positionable within slot (42) as described above. As shown in the illustrated example of FIG. 15, an upper pin (338) comprises a rectangular profile, such that upper pin (338) is positionable within lateral portions (347) of slot (342). Additionally, a firing beam (314) partially extends within top hat portion (355). Firing beam (314) and end effector (312) are operable to accomplish a cutting and stapling action in the same way as described above with respect to end effector (12) and firing beam (14).

As seen in the illustrated example of FIG. 15, anvil (318) further comprises stepped portions (349) along each outer side of anvil (318) and extending longitudinally. Each stepped portion (349) includes one row of staple forming pockets (353) in the present example. Stepped portions (349) are configured such that underside surface (326) of anvil (318) comprises stepped portions (349) as well as lower portions (351). As shown in FIG. 15, lower portions (351) are present along each side of longitudinally extending anvil slot (342), and lower portions (351) each include two rows of staple forming pockets (353). In the manner described above, stepped portions (349) are vertically offset from and parallel to lower portions (351) of anvil's (318)

underside surface (326). In view of the teachings herein, other configurations for underside surface (326) of anvil (318), and in particular stepped portions (349) and lower portions (351), will be apparent to those of ordinary skill in the art. For instance, in some examples the configuration for underside surface (326) complements the configuration of upper deck (372) of cartridge (337). For instance, cartridge (337) may have a multi-level upper deck (372) where raised portions coincide with vertically offset stepped portions (349).

Figure 16:
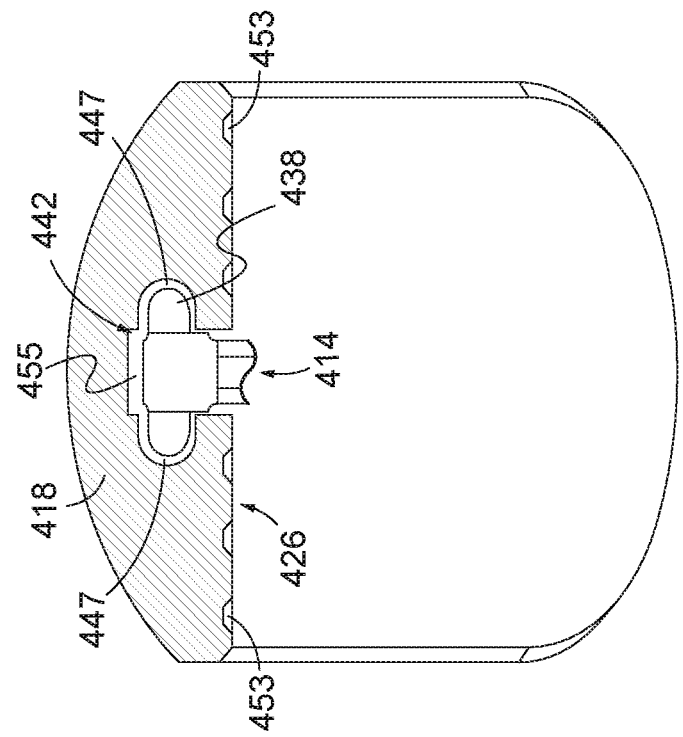
FIG. 16 depicts a cross-sectional view of an alternate version of an anvil for the end effector of FIG. 11, taken along a cross-sectional line similar view to line 15-15 of FIG. 12.

FIG. 16 depicts a section view of another exemplary anvil (418) for use with end effector (312). Anvil (418) is similar in all respects to anvil (318) except for its cross section as described here. In this way, anvil (318) may be modified to incorporate the cross section of anvil (418) described below instead of the cross section illustrated in FIG. 15. Anvil (418) comprises anvil slot (442). As shown, slot (442) comprises a partial "I" shape in cross section. The partial "I" shape of slot (442) is modified from that shown in FIG. 15 with respect to anvil slot (342). For anvil slot (442), slot (442) comprises lateral portions (447) and top hat portion (455). Whereas lateral portions (347) have a rectangular shape in profile with straight ends, lateral portions (447) have curved ends. Firing beam (414), which is similar to firing beam (14) described above, is positionable within slot (442) in the same manner as firing beam (14) is positionable within slot (42) as described above. As shown in the illustrated example of FIG. 16, an upper pin (438) comprises a matching profile to lateral portions (447) of slot (442), such that upper pin (438) is positionable within lateral portions (447) of slot (442). Additionally, a firing beam (414) partially extends within top hat portion (455), but to a lesser extent compared to firing beam (314) and top hat portion (355) of FIG. 15 as described above. Firing beam (414) and end effector (312) are operable to accomplish a cutting and stapling action in the same way as described above with respect to end effector (12) and firing beam (14).

With anvil (418) and slot (442), the clearance of top hat portion (455) is represented by the distance top hat portion (455) extends from lateral portion (447). With anvil (418) and slot (442), the clearance of top hat portion (455) is less compared to the clearance of top hat portion (355). Another difference between lateral portions (347) of anvil (318) and lateral portions (447) of anvil (418) is that the width of lateral portions (347) is greater than the width of lateral portions (447). This width of lateral portions (347, 447) defines the path within lateral portions (337, 447) for receiving and retaining respective pins (338, 438) as described above.

Anvil (418) also differs from anvil (318) as shown in FIGS. 15 and 16 in that anvil (418) lacks stepped portions (349) like in anvil (318). Instead anvil (418) comprises a uniformly planar underside surface (426), with slot (442) dividing underside surface (426) into two sides with each side having three rows of staple forming pockets (453). Furthermore, compared with anvil (318), anvil (418) comprises a slightly thinner profile where the distance from a top surface of anvil (418) to underside surface (426) is less compared to the same distance with anvil (318). In view of the teachings herein, it will be apparent to those of ordinary skill in the art, that in other versions, anvil (418) may be modified in terms of dimensions and/or to alter underside surface (426) to include stepped portions the same or similar to stepped portions (349) of anvil (318).

C. Exemplary Anvil Tips

In some instances, modifications can be made to the tip of the anvil to provide for possible further tissue capture benefits. Some such modifications or modified anvil tips are described below, and others will be apparent to those of ordinary skill in the art in view of the teachings herein.

Figure 17:
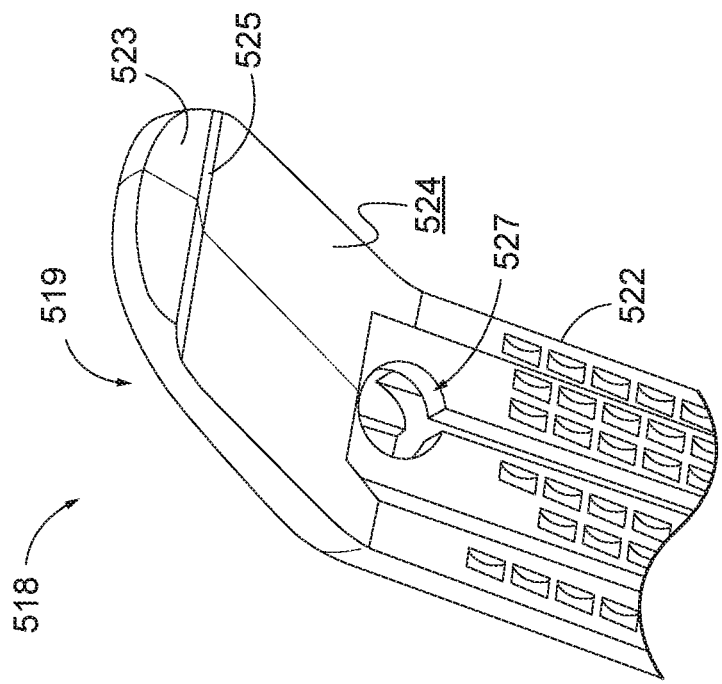
FIG. 17 depicts a partial perspective view of an alternate version of an anvil for the end effector of FIG. 11.

FIG. 17 illustrates another exemplary anvil (518) usable with end effector (312) in place of anvil (318). Anvil (518) comprises bent tip (519), which is similar to bent tip (319) as described above. Tip (519) comprises inner surface (524), which is similar to inner surface (324) described above. However, bent tip (519) further comprises projection (521) at its distal end. Projection (521) extends away from inner surface (524) toward cartridge (337) when in use. Projection (521) comprises a flat surface (523) configured to make contact with angled surface (341) of tip (339) of cartridge (337) when end effector (312) is closed. Projection (521) further comprises lip (525). Lip (525) extends transversely across the full width of tip (519).

When end effector (312) is closed, projection (521) is operable to promote tissue capture and prevent tissue from moving out from the distal end of end effector (312). By way of example, projection (521) provides for direct contact between tip (519) and tip (339) of cartridge (337), but at the same time provides for gap or space (345) proximal to the area of contact as described above. Space (345) provides a region where tissue can collect so as to not be squeezed out distally from the distal end of end effector (312). In examples using anvil (518) with its projection (521), gap or space (345) may be larger compared to examples of tips for anvils without projection (521). In other words, in some examples, but not necessarily required in all examples, when end effector (312) is closed, through contact with tip (339), projection (521) is configured to decrease the angle that a plane defined by inner surface (524) forms with plane (P1) defined by upper deck (372). Thus inner surface (524) is steeper relative to upper deck (372) compared to angled surface (341) of cartridge (337) relative to upper deck (372).

Tip (519) is further optionally configured as an insert to body portion (522) of anvil (518). In the present example, longitudinal slot (542) terminates with an opening (527) that is configured to receive a proximal member of tip (519) such that tip (519) is a rigid insert to body portion (522) of anvil (518). Some additional exemplary end effectors having curved anvil tips that are insertable within anvil body portions are described in U.S. patent application Ser. No. 15/435,607 entitled "Surgical Stapler with Insertable Distal Anvil Tip," filed on Feb. 17, 2017, published as U.S. Pub. No. 2018/0235610 on Aug. 23, 2018, and the disclosure of which is incorporated by reference herein; and also U.S. patent application Ser. 15/435,618 No. entitled "Surgical Stapler with Cooperating Distal Tip Features on Anvil and Staple Cartridge," filed on Feb. 17, 2017, published as U.S. Pub. No. 2018/0235611 on Aug. 23, 2018 and the disclosure of which is incorporated by reference herein. Of course in other versions, tip (519) is formed with anvil (518) as one piece and not an insert. In such instances opening (527) may be omitted.

Figure 18:
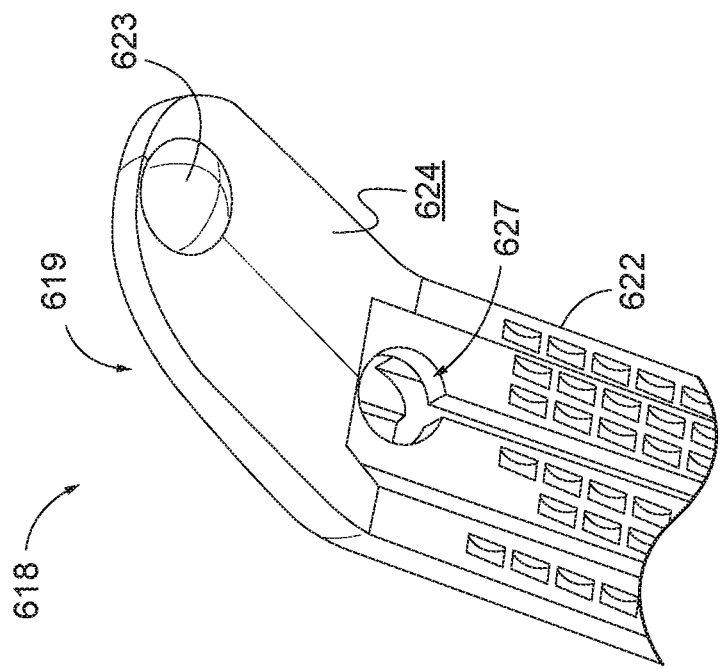
FIG. 18 depicts a partial perspective view of another alternate version of an anvil for the end effector of FIG. 11.

FIG. 18 illustrates another exemplary anvil (618) usable with end effector (312) in place of anvil (318). Anvil (618) comprises bent tip (619), which is similar to bent tip (319) as described above. Tip (619) comprises inner surface (624), which is similar to inner surface (324) described above. However, bent tip (619) further comprises projection (621) at its distal end. Projection (621) extends away from inner surface (624) toward cartridge (337) when in use. Projection (621) comprises a bulbous convex surface (623) that is configured to make contact with angled surface (341) of tip (339) of cartridge (337) when end effector (312) is closed.

When end effector (312) is closed, projection (621) is operable to promote tissue capture and prevent tissue from moving out from the distal end of end effector (312). By way of example, projection (621) provides for direct contact between tip (619) and tip (339) of cartridge (337), but at the same time provides for gap or space (345) proximal to the area of contact as described above. Space (345) provides a region where tissue can collect so as to not be squeezed out distally from the distal end of end effector (312). In examples using anvil (618) with its projection (621), gap or space (345) may be larger compared to examples of tips for anvils without projection (621). In other words, in some examples, but not necessarily required in all examples, when end effector (312) is closed, through contact with tip (339), projection (621) is configured to decrease the angle that a plane defined by inner surface (624) forms with plane (P1) defined by upper deck (372). Thus inner surface (624) is steeper relative to upper deck (372) compared to angled surface (341) of cartridge (337) relative to upper deck (372).

Tip (619) is further optionally configured as an insert to body portion (622) of anvil (618). In the present example, longitudinal slot (642) terminates with an opening (627) that is configured to receive a proximal member of tip (619) such that tip (619) is a rigid insert to body portion (622) of anvil (618). Some additional exemplary end effectors having curved anvil tips that are insertable within anvil body portions are described in U.S. patent application Ser. No. 15/435,607 entitled "Surgical Stapler with Insertable Distal Anvil Tip," filed on Feb. 17, 2017, published as U.S. Pub. No. 2018/0235610 on Aug. 23, 2018, and the disclosure of which is incorporated by reference herein; and also U.S. patent application Ser. No. 15/435,618 entitled "Surgical Stapler with Cooperating Distal Tip Features on Anvil and Staple Cartridge," filed on Feb. 17, 2017, published as U.S. Pub. No. 2018/0235611 on Aug. 23, 2018, and the disclosure of which is incorporated by reference herein. Of course in other versions, tip (619) is formed with anvil (618) as one piece and not an insert. In such instances opening (627) may be omitted.

In view of the teachings herein, other ways to modify tips (319, 519, 619) of respective anvils (318, 518, 618) to provide for either a uniform flat surface or for one or more projections as described above will be apparent to those of ordinary skill in the art. As will be understood in view of the teachings herein, the angle associated with bent tips of anvils, and/or additional features like projections described above, can aid in tissue capture, which also benefits marching applications as described above.

D. Exemplary Cartridge Options

As will be described further below, with end effectors that incorporate rigid bent anvil tips, enhanced tissue gripping can be achieved using end effectors having anvil tips and cartridge noses with cooperating features. Such cooperating features may provide a lock or tissue stop that prevents clamped tissue from moving distally out of the distal end of the end effector during a cutting and stapling action. Such cooperating features may also act as a tactile feedback feature to signal to a user that they have completely clamped the tissue, vessel, or tubular structure by feeling the cooperating features engage or contact at the distal end. In marching applications, such cooperating features can similarly act as a feedback feature or structure to signal to a user that they are at the end of the tissue path, as evidenced by the cooperating features engaging or contacting at the distal end (as opposed to the respective cooperating features each contacting tissue). Also, in some instances, modifications can be made to the cartridge upper deck configuration to provide for possible enhancements in cutting and stapling. Some such modifications or modified cartridges are described below, and others will be apparent to those of ordinary skill in the art in view of the teachings herein.

Figure 19:
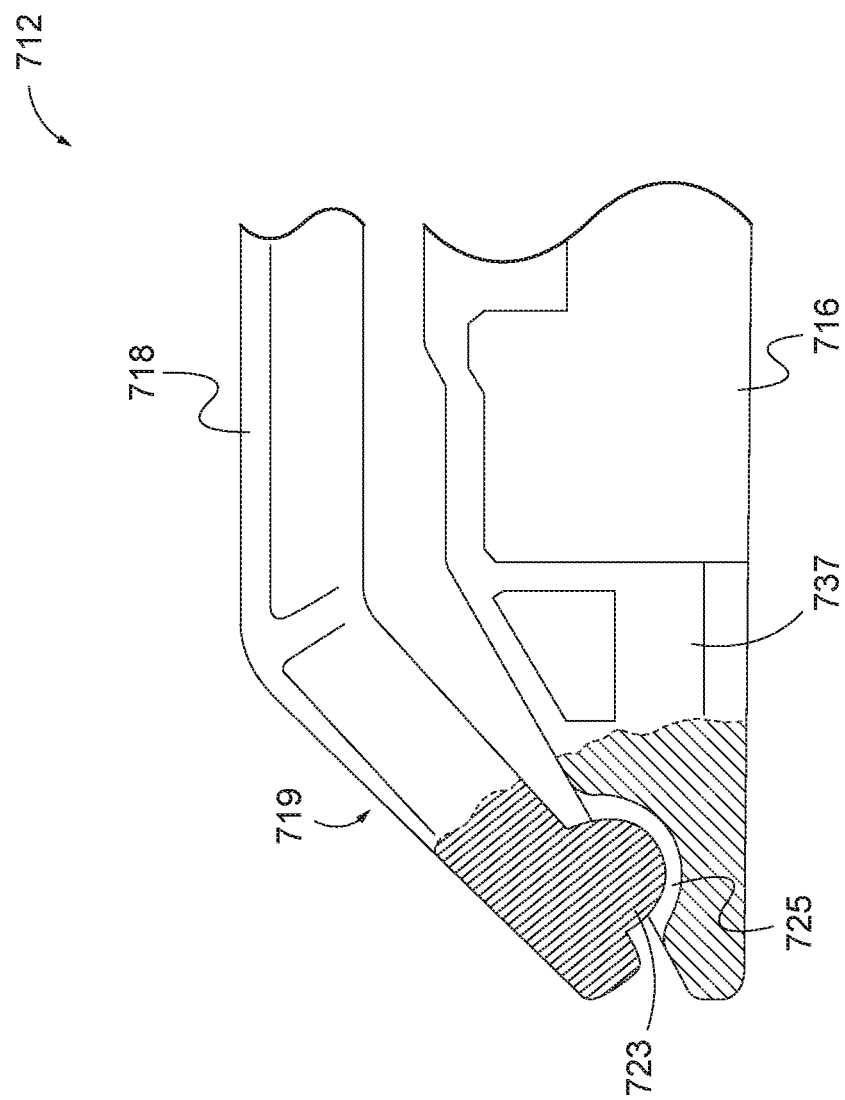
FIG. 19 depicts an enlarged side view of the distal portion of an alternate version of an end effector having cooperating rigid anvil tip and cartridge tip features.

FIG. 19 depicts a distal portion of another exemplary end effector (712) comprising anvil (718), lower jaw (716), and cartridge (737). It will be appreciated that end effector (712) may be used in place of end effector (12) of instrument (10). End effector (712) may be integrally formed with instrument (10) or in the alternative may be interchangeable with end effector (12) of instrument (10). Anvil (718) is operable to pivot relative to lower jaw (716). Anvil (718) and lower jaw (716) may clamp tissue (90) similarly to clamping performed by anvil (18) and lower jaw (16) shown in FIG. 1. Cartridge (737) is operable to be placed in lower jaw (716) similarly to cartridge (37) shown in FIG. 3.

Anvil (718) comprises bent tip (719), which is similar to tip (619) described above where tip (719) comprises bulbous convex surface (723). Cartridge (737) comprises a ball-shaped cut-out or recess (725) that is shaped to complement surface (723). In the present example, rigid bulbous surface (723) of tip (719) and recess (725) are cooperating features configured to promote tissue capture. In one version, end effector (712) is configured such that when end effector (712) is closed, rigid anvil tip (719) with bulbous surface (723) does not contact cartridge (737). In such instances, when clamping tissue in a marching application, bulbous surface (723) of anvil tip (719) may push tissue (90) within recesses (725) and retain tissue (90) there under compression to provide for secure tissue capture during a cutting and stapling operation. Still in other versions, end effector (712) may be configured such that bulbous surface (723) contacts recess (725) when clamping. In such instances, when clamping tissue in a marching application, tactilely detected contact between bulbous surface (723) and recess (725) may act as a feedback feature for detecting the final cut in the marching operation as discussed above. In view of the teachings herein, shapes other than bulbous surface (723) and ball-shaped cut-out (725) may be used to provide for similar functionality, and such other shapes or modifications will be apparent to those of ordinary skill in the art in view of the teachings herein.

Figure 20:
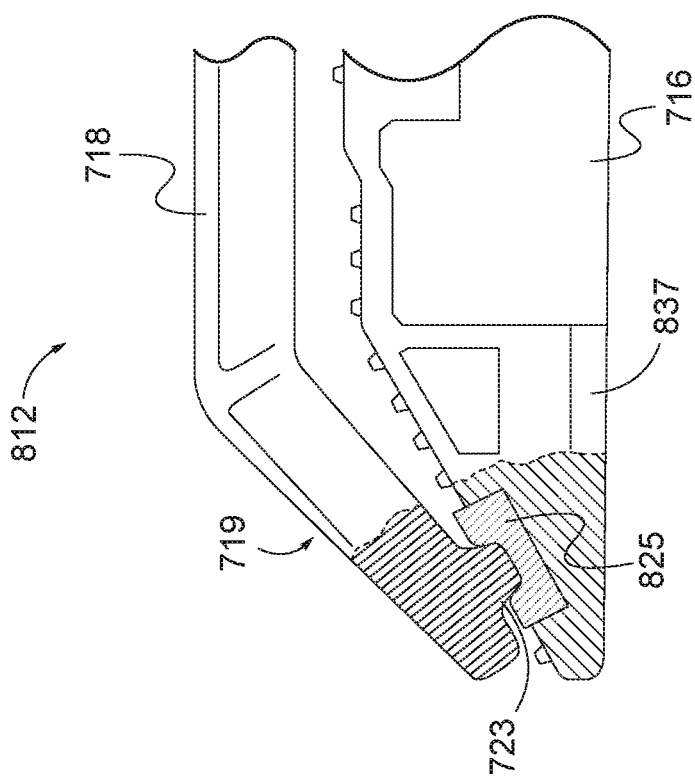
FIG. 20 depicts an enlarged side view of the distal portion of an alternate version of an end effector incorporating additional gripping features on the cartridge and used with an anvil having a rigid bent tip.

FIG. 20 depicts a distal portion of another exemplary end effector (812) comprising anvil (718) and lower jaw (716) as described above. End effector (812) further comprises cartridge (837). It will be appreciated that end effector (812) may be used in place of end effector (12) of instrument (10). End effector (812) may be integrally formed with instrument (10) or in the alternative may be interchangeable with end effector (12) of instrument (10). Anvil (718) is operable to pivot relative to lower jaw (716). Anvil (718) and lower jaw (716) may clamp tissue (90) similarly to clamping performed by anvil (18) and lower jaw (16) shown in FIG. 1. Cartridge (837) is operable to be placed in lower jaw (716) similarly to cartridge (37) shown in FIG. 3.

Anvil (718) comprises bent tip (719), which is similar to tip (619) described above where tip (719) comprises bulbous surface (723). Cartridge (837) comprises a pad (825) constructed of a flexible elastomer such that pad (825) is resilient. In the present example, rigid bulbous surface (723) of tip (719) and pad (825) are cooperating features configured to promote tissue capture. In one version without tissue present, or when clamped tissue is positioned within only the straight portions of end effector (812), end effector (812) is configured such that when end effector (812) is closed, rigid anvil tip (719) with bulbous surface (723) contacts cartridge (837), and specifically bulbous surface (723) contacts pad (825) as shown in FIG. 20. In other instances, when clamping tissue in a marching application, bulbous surface (723) of anvil tip (719) may compress tissue (90) against pad (825) to provide for secure tissue capture during a cutting and stapling operation. In such marching applications, when at the end of the tissue cut line, the contact between bulbous surface (723) and pad (825) can be felt by the user such that these structures may act as a feedback feature for detecting the final cut in the marching operation as discussed above. Still in other versions, end effector (812) may be configured such that bulbous surface (723) does not contact pad (825) when clamping whether or not tissue is present. In view of the teachings herein, shapes other than bulbous surface (723) and features other than pad (825) may be used to provide for similar functionality, and such other shapes, features, or modifications will be apparent to those of ordinary skill in the art in view of the teachings herein.

Figure 21:
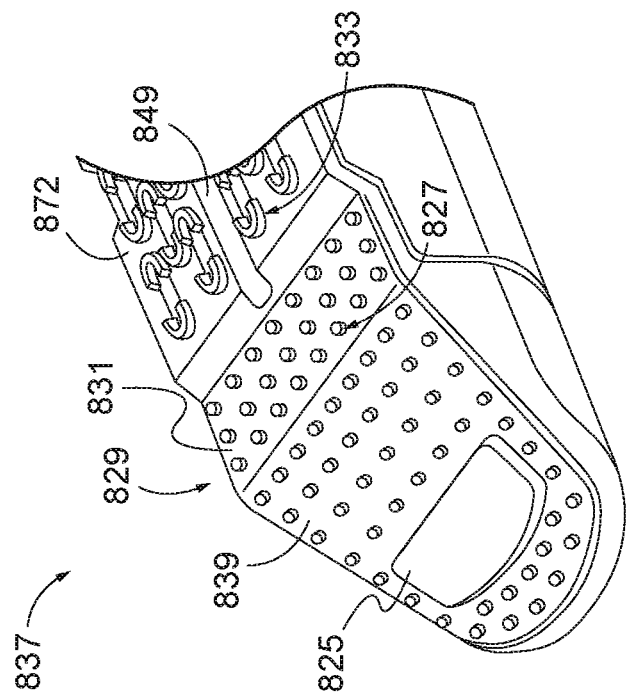
FIG. 21 depicts an enlarged perspective view of the distal portion of the cartridge of the end effector of FIG. 20.

FIG. 21 depicts a closer view of cartridge (837). As shown in this illustrated version, cartridge (837) comprises a plurality of raised features (827) located on a nose portion (829) of cartridge (837). In the present example, nose portion (829) comprises distal tip (839) of cartridge (837), which is angled, along with a lower deck portion (831) that extends parallel with upper deck (872) of cartridge (837). Raised features (827) generally cover the top surface of nose portion (829) and are evenly spaced. In the present example, raised features (827) are rigid and comprise projecting cylindrical members; however, in other versions raised features (827) can be rigid raised bumps or have any other suitable shape that projects from the top surface of nose portion (829). As shown in FIG. 21 raised features (827) generally surround pad (825), which is flexible as described above. Still in some other versions, surface texture may be imparted to nose portion (829) by having a plurality of recesses or etchings in the surface of nose portion (829).

Cartridge (837) further comprises a plurality of raised features (833) located on upper deck (872) of cartridge (837). Raised features (833) extend along both slides of vertical slot (849). In the present example, raised features (833) are rigid and provide for enhanced gripping of tissue. It should be understood that both raised features (827, 833) may be referred to as gripping features. Raised features (833) are configured in the illustrated version as pairs of U-shaped members where each of the members faces the other. In view of the teachings herein, other shapes and configurations for raised features (833) will be apparent to those of ordinary skill in the art. Furthermore, while the present example shows cartridge (837) as having both raised features (827, 833), in other versions cartridge (837) may have only raised features (827). Still in other versions, cartridge (837) may have only raised features (833). Still yet, in other versions, cartridge (837) may have neither raised features (827, 833) similar to cartridge (37) for instance.

Figure 22:
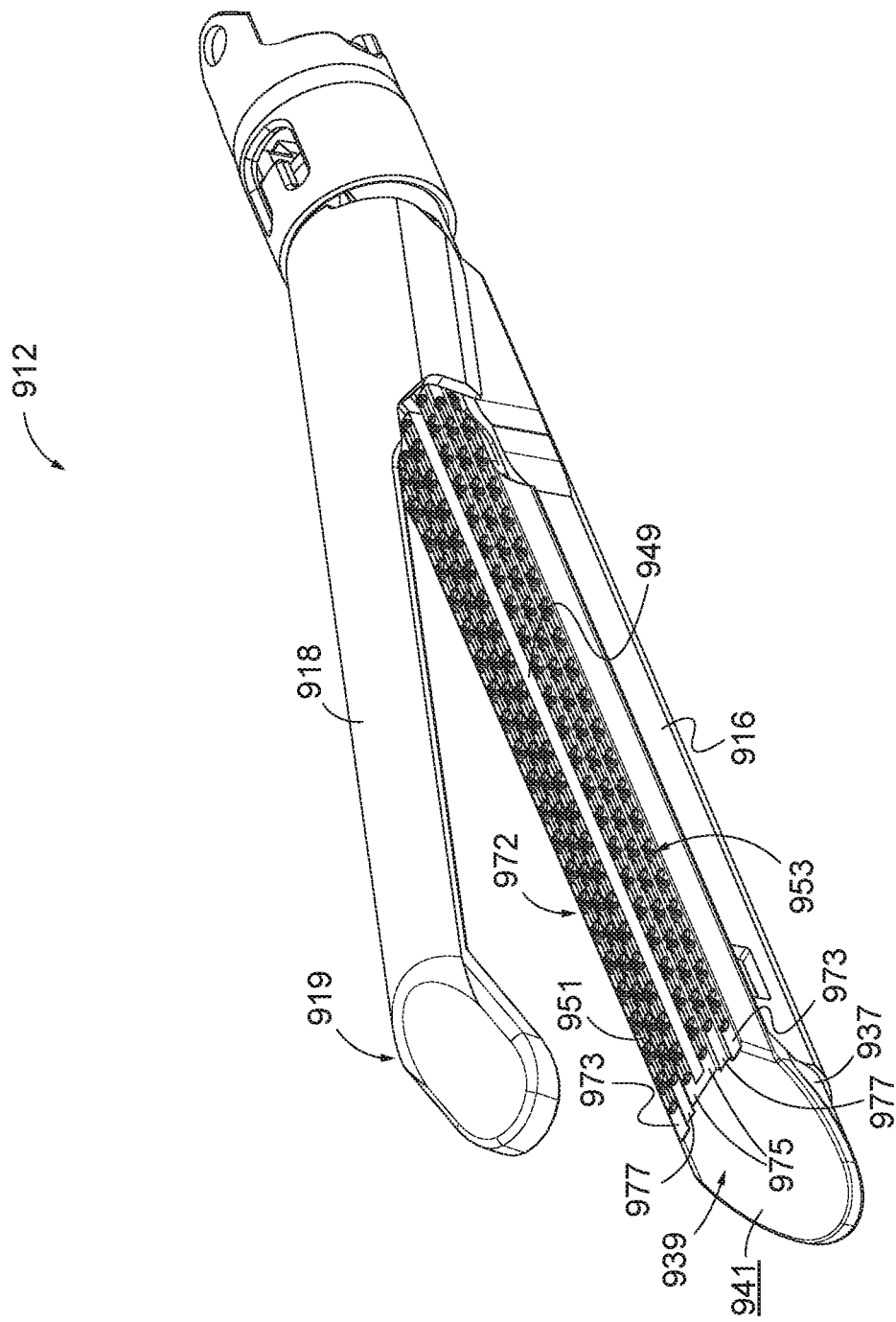
FIG. 22 depicts a perspective view of a distal portion of an alternative version of an end effector, with a curved anvil tip, shown in an open configuration.

FIG. 22 depicts another exemplary end effector (912) comprising anvil (918), lower jaw (916), and cartridge (937). It will be appreciated that end effector (912) may be used in place of end effector (12) of instrument (10). End effector (912) may be integrally formed with instrument (10) or in the alternative may be interchangeable with end effector (12) of instrument (10). Anvil (918) is operable to pivot relative to lower jaw (916). Anvil (918) and lower jaw (916) may clamp tissue (90) similarly to clamping performed by anvil (18) and lower jaw (16) shown in FIG. 1. Cartridge (937) is operable to be placed in lower jaw (916) similarly to cartridge (37) shown in FIG. 3. Alternatively, in some versions where end effector (912) is removable from the rest of instrument (10), cartridge (937) may be permanently fixed in lower jaw (916).

As shown in FIG. 22, end effector (912) combines anvil (918) having a bent tip (919) with cartridge (937) having an angled surface (941) along a distal tip (939) of cartridge (937), similar to the configuration of end effector (312) described above. In the present example, end effector (912) includes further features, and specifically a multi-level staple deck (972) of cartridge (937). In the illustrated version, multi-level staple deck (972) comprises three levels located along each side of a vertical slot (949) that bisects cartridge (937) longitudinally. An outer level (973) on each side includes one row of staple apertures (951) that extend longitudinally along the surface of cartridge (937). An inner level (975) on each side includes one row of staple apertures (951) that extend longitudinally along the surface of cartridge (937). And lastly a middle level (977) on each side, between outer level (973) and inner level (975), includes one row of staple apertures (951) that extend longitudinally along the surface of cartridge (937). As illustrated, outer levels (973) of multi-level staple deck (972) are offset from middle levels (977). Middle levels (977) of multi-level staple deck (972) are offset from inner levels (975). In the present example, the offset of the levels is configured in a stair-step manner with a step up from one level to the next as the levels approach vertical slot (949). In view of the teachings herein, other ways to configure multi-level staple deck (972) will be apparent to those of ordinary skill in the art.

In the present example, multi-level staple deck (972) of cartridge (937) comprises a plurality of raised features (953) that are the same in configuration as raised features (833) described above with respect to end effector (812). As described above, raised features (953) are configured to provide for improved tissue capture and gripping. While cartridge (937) includes raised features (953) in the present example, in other versions raised features (953) may be omitted such that multi-level staple deck (972) comprises a flat surface along each level. Additionally, in the present example, angled surface (941) is shown as flat, but in other versions angled surface (941) may include raised features (827) as described above. In view of the teachings herein, other ways to configure end effector (912) will be apparent to those of ordinary skill in the art.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus, comprising: (a) a body portion; (b) a shaft extending distally from the body portion; and (c) an end effector in communication with the shaft, wherein the end effector is movable between an open configuration and a closed configuration, wherein the end effector is operable to compress, staple, and cut tissue, and wherein the end effector comprises: (i) a cartridge configured to hold one or more staples, wherein the cartridge comprises a nose portion having an angled surface, (ii) an anvil comprising a proximal body portion and a tip extending distally from the body portion, wherein the tip comprises a bent configuration, and (iii) a plurality of gripping features positioned along a staple deck of the cartridge, wherein the plurality of gripping features are configure to contact tissue grasped between the end effector when in the closed configuration.

EXAMPLE 2

The apparatus of Example 1, wherein the tip comprising the bent configuration is rigid.

EXAMPLE 3

The apparatus of any one or more of Examples 1 through 2, wherein the nose portion of the cartridge comprises a curved underside.

EXAMPLE 4

The apparatus of any one or more of Examples 1 through 3, wherein the nose portion of the cartridge comprises a first blunt end, and wherein the tip of the anvil comprises a second blunt end.

EXAMPLE 5

The apparatus of Example 4, wherein when the end effector is in the closed configuration, the second blunt end is longitudinally aligned with the first blunt end.

EXAMPLE 6

The apparatus of any one or more of Examples 1 through 5, wherein the tip comprises an inner surface, wherein when the end effector is in the closed configuration, a distal portion of the inner surface is configured to contact the angled surface of the nose portion of the cartridge when tissue is not present within the end effector.

EXAMPLE 7

The apparatus of Example 6, wherein the inner surface of the tip has an angled configuration.

EXAMPLE 8

The apparatus of any one or more of Examples 6 through 7, wherein when the end effector is in the closed configuration without tissue present within the end effector, the inner surface of the tip and the angled surface of the nose portion of the cartridge are configured to define a space therebetween.

EXAMPLE 9

The apparatus of any one or more of Examples 1 through 8, wherein the staple deck defines a first plane, wherein the tip comprises an inner surface that defines a second plane, and wherein the angled surface of the nose portion defines a third plane, wherein the second plane and the third plane are not co-planar.

EXAMPLE 10

The apparatus of Example 9, wherein a first angle formed by a first intersection of the second plane with the first plane is larger than a second angle formed by a second intersection of the third plane with the first plane.

EXAMPLE 11

The apparatus of any one or more of Examples 9 through 10, wherein the inner surface of the tip is steeper compared to the angled surface of the nose portion.

EXAMPLE 12

The apparatus of any one or more of Examples 1 through 11, wherein the tip of the anvil comprises a projection at a distal end of the tip.

EXAMPLE 13

The apparatus of Example 12, wherein the projection comprises a flat portion configured to contact the angled surface of the nose portion when the end effector is in the closed configuration.

EXAMPLE 14

The apparatus of Example 12, wherein the projection comprises a bulbous member.

EXAMPLE 15

The apparatus of Example 14, wherein the angled surface of the nose portion comprises a complementary feature to the bulbous member of the tip.

EXAMPLE 16

The apparatus of any one or more of Examples 1 through 15, wherein the staple deck of the cartridge comprises a multi-level staple deck.

EXAMPLE 17

An apparatus, comprising: (a) a body portion; (b) a shaft extending distally from the body portion; and (c) an end effector in communication with the shaft, wherein the end effector is movable between an open configuration and a closed configuration, wherein the end effector is operable to compress, staple, and cut tissue, and wherein the end effector comprises: (i) a cartridge configured to hold one or more staples, wherein the cartridge comprises a staple deck and a nose portion having an angled surface, wherein the angled surface comprises a resilient pad, and (ii) a rigid anvil comprising a proximal body portion and a tip extending distally from the body portion, wherein the tip comprises a bent configuration, wherein the tip further comprises a projection configured to contact the pad when the end effector is in the closed configuration without tissue present within the end effector.

EXAMPLE 18

The apparatus of Example 17, wherein the end effector further comprises a first plurality of gripping features positioned along the staple deck of the cartridge, and a second plurality of gripping features positioned along the angled surface of the nose portion, wherein the first and second pluralities of gripping features are configured to contact tissue grasped between the end effector when in the closed configuration.

EXAMPLE 19

The apparatus of any one or more of Examples 17 through 18, wherein the anvil comprises an underside surface comprising a plurality of staple forming pockets, wherein the underside surface further comprises at least one stepped portion.

EXAMPLE 20

An apparatus, comprising: (a) a body portion; (b) a shaft extending distally from the body portion; and (c) an end effector in communication with the shaft, wherein the end effector is movable between an open configuration and a closed configuration, wherein the end effector is operable to compress, staple, and cut tissue, and wherein the end effector comprises: (i) a cartridge configured to hold one or more staples, wherein the cartridge comprises a staple deck and a nose portion, wherein the nose portion comprises an angled surface, and wherein the staple deck comprises a plurality of gripping features configured to contact tissue grasped between the end effector when in the closed configuration, and (ii) an anvil comprising a proximal body portion and a tip extending distally from the body portion, wherein the tip comprises a bent configuration, wherein the body portion comprises a longitudinal slot having a partial "I" shaped profile with lateral portions having curved ends configured to receive a pin of a firing beam.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. patent application Ser. No. 29/594,332, entitled "Surgical Stapler End Effector with Varying Deck Height and Tissue Gripping Features," filed on Feb. 17, 2017, issued as U.S. Pat No. D836,198 on Dec. 18, 2018, the disclosure of which is incorporated by reference herein. Various suitable ways in which the teachings herein may be combined with the teachings of U.S. patent application Ser. No. 29/594,332 filed on Feb. 17, 2017, issued as U.S. Pat. No. D836,198 on Dec. 18, 2018, will be apparent to those of ordinary skill in the art.

It should also be understood that the teachings herein may be readily combined with various teachings in U.S. patent application Ser. No. 29/594,335, entitled "Circular Surgical Stapler End Effector with Varying Deck Height and Tissue Gripping Features," filed on Feb. 17, 2017, issued at U.S. Pat. No. D833,010 on Nov. 6, 2018, the disclosure of which is incorporated by reference herein. Various suitable ways in which the teachings herein may be combined with the teachings of U.S. patent application Ser. No. 29/594,335 filed on Feb. 17, 2017, issued as U.S. Pat. No. D833,010 on Nov. 6, 2018, will be apparent to those of ordinary skill in the art.

It should also be understood that the teachings herein may be readily combined with various teachings in U.S. patent application Ser. No. 15/435,573, entitled "Surgical Stapler with Elastically Deformable Tip," filed on Feb. 17, 2017, published as U.S. Pub. No. 2018/0235609 on Aug. 23, 2018, the disclosure of which is incorporated by reference herein. Various suitable ways in which the teachings herein may be combined with the teachings of U.S. patent application Ser. No. 15/435,573 filed on Feb. 17, 2017, published as U.S. Pub. No. 2018/0235609 on Aug. 23, 2018, will be apparent to those of ordinary skill in the art.

It should also be understood that the teachings herein may be readily combined with various teachings in U.S. patent application Ser. No. 15/435,607, entitled "Surgical Stapler with Insertable Distal Anvil Tip," filed on Feb. 17, 2017, published as U.S. Pub. No. 2018/0235610 on Aug. 23, 2018, the disclosure of which is incorporated by reference herein. Various suitable ways in which the teachings herein may be combined with the teachings of U.S. patent application Ser. No. 15/435,607 filed on Feb. 17, 2017, published as U.S. Pub. No. 2018/0235610 on Aug. 23, 2018, will be apparent to those of ordinary skill in the art.

It should also be understood that the teachings herein may be readily combined with various teachings in U.S. Patent App. No. 15/435,618, entitled "Surgical Stapler with Cooperating Distal Tip Features on Anvil and Staple Cartridge," filed on Feb. 17, 2017, published as U.S. Pub. No. 2018/0235611 on Aug. 23, 2018, the disclosure of which is incorporated by reference herein. Various suitable ways in which the teachings herein may be combined with the teachings of U.S. patent application Ser. No. 15/435,618 filed on Feb. 17, 2017, published as U.S. Pub. No. 2018/0235611 on Aug. 23, 2018, will be apparent to those of ordinary skill in the art.

It should also be understood that the teachings herein may be readily combined with various teachings in U.S. patent application Ser. No. 29/594,340, entitled "Surgical Stapler with Bent Anvil Tip and Angled Staple Cartridge Tip," filed on Feb. 17, 2017, issued as U.S. Pat. No. D836,199 on Dec. 18, 2018, the disclosure of which is incorporated by reference herein. Various suitable ways in which the teachings herein may be combined with the teachings of U.S. patent application Ser. No. 29/594,340 filed on Feb. 17, 2017, issued as U.S. Pat. No. D836,199 on Dec. 18, 2018, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

(a) a body portion;

(b) a shaft extending distally from the body portion; and (c) an end effector in communication with the shaft, wherein the end effector is movable between an open configuration and a closed configuration, wherein the end effector is operable to compress, staple, and cut tissue, and wherein the end effector comprises:
  (i) a cartridge configured to hold one or more staples, wherein the cartridge comprises a nose portion having an angled nose surface,
  (ii) an anvil comprising a proximal body portion and a tip extending distally from the body portion, wherein an underside of the body portion includes an anvil surface having a plurality of staple forming pockets, wherein the tip is bent relative to the proximal body portion and includes an underside that defines an angled tip surface, wherein an entirety of the angled tip surface is angled relative to the anvil surface, wherein when the end effector is in the closed configuration the angled tip surface is configured to confront the angled nose surface such that an entirety of the angled tip surface is angled relative to the angled nose surface and such that a proximal end of the angled tip surface is positioned proximal to a proximal end of the angled nose surface, and
  (iii) a plurality of gripping features positioned along a staple deck of the cartridge, wherein the gripping features are configured to contact tissue grasped between the end effector when in the closed configuration.

2. The apparatus of claim 1, wherein the tip comprising the bent configuration is rigid.

3. The apparatus of claim 1, wherein the nose portion of the cartridge comprises a curved underside.

4. The apparatus of claim 1, wherein the nose portion of the cartridge comprises a first blunt end, and wherein the tip of the anvil comprises a second blunt end.

5. The apparatus of claim 1, wherein when the end effector is in the closed configuration, a distal end of the nose portion of the cartridge is longitudinally aligned with a distal end of the tip of the anvil in a plane that extends transversely to a longitudinal axis of the end effector.

6. The apparatus of claim 1, wherein when the end effector is in the closed configuration, a distal portion of the angled tip surface is configured to contact the angled nose surface of the nose portion of the cartridge when tissue is not present within the end effector.

7. The apparatus of claim 6, wherein the angled tip surface is angled distally toward a longitudinal axis of the cartridge.

8. The apparatus of claim 6, wherein when the end effector is in the closed configuration without tissue present within the end effector, the angled tip surface and the angled nose surface are configured to define a space therebetween, wherein the space tapers distally.

9. The apparatus of claim 1, wherein the staple deck extends along a flat first plane, wherein an entirety of the angled tip surface extends along a flat second plane that is angled relative to the first plane, and wherein an entirety of the angled nose surface of the nose portion extends along a flat third plane, wherein the second plane and the third plane are not co-planar.

10. The apparatus of claim 9, wherein a first angle formed by a first intersection of the second plane with the first plane is larger than a second angle formed by a second intersection of the third plane with the first plane.

11. The apparatus of claim 9, wherein the second plane is steeper relative to the first plane than relative to to the third plane.

12. The apparatus of claim 1, wherein the tip of the anvil comprises a projection at a distal end of the tip.

13. The apparatus of claim 12, wherein the projection comprises a flat portion configured to contact the angled nose surface of the nose portion when the end effector is in the closed configuration.

14. The apparatus of claim 12, wherein the projection comprises a bulbous member.

15. The apparatus of claim 14, wherein the angled nose surface of the nose portion comprises a complementary feature to the bulbous member of the tip.

16. The apparatus of claim 1, wherein the tip of the anvil is integrally formed with the proximal body portion of the anvil.

17. An apparatus, comprising:
(a) a body portion;
(b) a shaft extending distally from the body portion; and
(c) an end effector in communication with the shaft, wherein the end effector is movable between an open configuration and a closed configuration, wherein the end effector is operable to compress, staple, and cut tissue, and wherein the end effector comprises:
  (i) a cartridge configured to hold one or more staples, wherein the cartridge comprises a staple deck and a nose portion having an angled surface, wherein the angled surface comprises a resilient pad spaced proximally from a distal-most end of the nose portion, and
  (ii) an anvil comprising a proximal body portion and a tip extending distally from the body portion, wherein the tip comprises a bent configuration, wherein the tip further comprises a projection spaced proximally from a distal-most end of the tip, wherein the tip is configured to align with and contact the pad when the end effector is in the closed configuration without tissue present within the end effector.

18. The apparatus of claim 17, wherein the end effector further comprises a first plurality of gripping features positioned along the staple deck of the cartridge, and a second plurality of gripping features positioned along the angled surface of the nose portion, wherein at least some of the second plurality of gripping features are positioned distal to the pad, wherein the first and second pluralities of gripping features are configured to contact tissue grasped between the end effector when in the closed configuration.

19. The apparatus of claim 17, wherein the anvil comprises an underside surface comprising a plurality of staple forming pockets, wherein the underside surface further comprises at least one stepped portion.

20. An apparatus, comprising:
(a) a body portion;
(b) a shaft extending distally from the body portion; and
(c) an end effector in communication with the shaft, wherein the end effector is movable between an open configuration and a closed configuration, wherein the end effector is operable to compress, staple, and cut tissue, and wherein the end effector comprises:
  (i) a cartridge configured to hold one or more staples, wherein the cartridge comprises a staple deck and a nose portion, wherein the nose portion comprises an angled surface, and wherein the staple deck comprises a plurality of gripping features configured to contact tissue grasped between the end effector when in the closed configuration, and
  (ii) an anvil comprising a proximal body portion and a tip extending distally from the body portion, wherein the tip comprises a bent configuration, wherein the body portion comprises an anvil surface having a plurality of staple forming pockets, wherein the body portion further comprises a longitudinal slot having a longitudinally open proximal end and a longitudinally closed distal end, wherein the longitudinal slot has a partial "I" shaped profile with lateral portions having curved ends configured to receive a pin of a firing beam such that curved ends of the pin are slidably disposed within the curved ends of the longitudinal slot, wherein each curved end of the longitudinal slot is symmetrical about a plane that extends parallel to the anvil surface and through the curved ends of the longitudinal slot.

* * * * *